US008202512B2

(12) United States Patent
McCleary

(10) Patent No.: US 8,202,512 B2
(45) Date of Patent: Jun. 19, 2012

(54) METABOLIC UNCOUPLING THERAPY

(76) Inventor: Edward Larry McCleary, Incline Village, NV (US)

(*) Notice: Subject to any disclaimer, the term of this patent is extended or adjusted under 35 U.S.C. 154(b) by 0 days.

(21) Appl. No.: 13/198,289

(22) Filed: Aug. 4, 2011

(65) Prior Publication Data

US 2011/0293588 A1    Dec. 1, 2011

Related U.S. Application Data

(60) Division of application No. 11/703,446, filed on Feb. 6, 2007, now abandoned, which is a division of application No. 10/462,958, filed on Jun. 17, 2003, now abandoned, which is a continuation-in-part of application No. 09/749,584, filed on Dec. 28, 2000, now Pat. No. 6,579,866.

(51) Int. Cl.
*A61K 47/06* (2006.01)
*A61K 38/43* (2006.01)
*A61K 127/00* (2006.01)
*A61K 9/50* (2006.01)
*A61K 65/00* (2006.01)

(52) U.S. Cl. ............ 424/78.02; 424/502; 424/729; 424/745; 424/94.1

(58) Field of Classification Search ........... 424/78.02, 424/502, 729, 754, 94.1
See application file for complete search history.

(56) References Cited

U.S. PATENT DOCUMENTS

| | | | |
|---|---|---|---|
| 4,599,232 A | 7/1986 | Bertelli | |
| 4,812,447 A | 3/1989 | Roberts | |
| 5,104,880 A | 4/1992 | Kozikowski | |
| 5,397,786 A | 3/1995 | Simone | |
| 5,411,945 A | 5/1995 | Ozaki et al. | |
| 5,436,269 A | 7/1995 | Yazawa et al. | |
| 5,518,902 A | 5/1996 | Ozaki et al. | |
| 5,560,928 A | 10/1996 | DeFelice | |
| 5,626,849 A | 5/1997 | Hastings et al. | |
| 5,668,117 A | 9/1997 | Shapiro | |
| 5,716,614 A | 2/1998 | Katz et al. | |
| 5,744,161 A | 4/1998 | Majeed et al. | |
| 5,895,652 A | 4/1999 | Giampapa | |
| 5,914,326 A | 6/1999 | McCarty et al. | |
| 5,948,430 A | 9/1999 | Zerbe et al. | |
| 5,972,357 A | 10/1999 | Yamaguchi et al. | |
| 5,973,004 A | 10/1999 | Howard | |
| 6,020,139 A | 2/2000 | Schwartz et al. | |
| 6,020,378 A | 2/2000 | Cook et al. | |
| 6,048,846 A | 4/2000 | Cochran | |
| 6,063,820 A | 5/2000 | Cavazza | |
| 6,117,872 A | 9/2000 | Maxwell et al. | |
| 6,133,317 A | 10/2000 | Hart | |
| 6,156,355 A | 12/2000 | Shields, Jr. et al. | |
| 6,277,396 B1 | 8/2001 | Dente | |
| 6,277,842 B1 | 8/2001 | Carthron | |
| 6,346,267 B1 | 2/2002 | Fry et al. | |
| 6,368,617 B1 | 4/2002 | Hastings et al. | |
| 6,475,530 B1 | 11/2002 | Kuhrts | |
| 6,488,957 B1 | 12/2002 | Koumarianos | |
| 6,492,429 B1 | 12/2002 | Graus et al. | |
| 6,541,045 B1 | 4/2003 | Charters et al. | |
| 6,572,897 B1 | 6/2003 | Gorsek | |
| 6,579,866 B2 | 6/2003 | McCleary | |
| 6,596,298 B2 | 7/2003 | Leung et al. | |
| 6,630,192 B2 | 10/2003 | Sundram et al. | |
| 6,645,472 B1 | 11/2003 | Anderson | |
| 6,656,493 B2 | 12/2003 | Dzija et al. | |
| 6,849,281 B2 | 2/2005 | Bodor et al. | |
| 6,896,890 B2 * | 5/2005 | Singh et al. | 424/401 |
| 7,445,807 B2 | 11/2008 | Lockwood | |
| 2001/0007868 A1 | 7/2001 | Facchini | |
| 2002/0002146 A1 | 1/2002 | Halevie-Goldman | |
| 2002/0018832 A1 | 2/2002 | Wong et al. | |
| 2002/0122834 A1 | 9/2002 | Trant | |
| 2002/0142052 A1 | 10/2002 | Trant | |
| 2002/0146463 A1 | 10/2002 | Clayton | |
| 2002/0182196 A1 | 12/2002 | McCleary | |
| 2002/0183263 A1 | 12/2002 | Hageman et al. | |
| 2003/0031758 A1 | 2/2003 | Koss et al. | |
| 2003/0039723 A1 | 2/2003 | Park | |
| 2003/0054058 A1 | 3/2003 | Corley et al. | |
| 2003/0108645 A1 | 6/2003 | Armand et al. | |
| 2003/0139354 A1 | 7/2003 | Buccholz et al. | |
| 2003/0170643 A1 | 9/2003 | Fisher et al. | |
| 2003/0185918 A1 | 10/2003 | Rosenbloom | |
| 2003/0206978 A1 | 11/2003 | Sherwood et al. | |
| 2003/0232091 A1 * | 12/2003 | Shefer et al. | 424/490 |
| 2004/0043013 A1 | 3/2004 | McCleary | |
| 2004/0072765 A1 | 4/2004 | Kelly et al. | |
| 2004/0081681 A1 * | 4/2004 | Vromen | 424/449 |
| 2004/0136922 A1 | 7/2004 | Leung et al. | |
| 2004/0220137 A1 * | 11/2004 | Sauermann | 514/54 |
| 2005/0002992 A1 | 1/2005 | McCleary et al. | |
| 2005/0025812 A1 | 2/2005 | Forest | |
| 2006/0039971 A1 | 2/2006 | Lee et al. | |

FOREIGN PATENT DOCUMENTS

| | | |
|---|---|---|
| GB | 2370504 | 7/2002 |
| RU | 2205655 C1 | 6/2003 |
| WO | WO-2006017551 A1 | 2/2006 |

OTHER PUBLICATIONS

Duke, Ph.D., "The Green Pharmacy: anti-aging Prescriptions," *Rodale*, 2001; 92-93.
http://web.archive.org/web/*/http://www.pcrm.org/resch/anexp/rats.html (Web Publication Date: Feb. 27, 2003). Dated accessed: Apr. 19, 2007.
Krafte et al., "Hydrogen Ion Modulation of Ca Channel Current in Cardiac Ventricular Cells," *J. Gen. Physiol.*, The Rockefeller University Press, 1988; 91:641-657.
Schweiz et al.; "Latent Acidosis: Over acidification as a Cause of Chronic Diseases"; Journal Suisse de medecine globale; vol. 14; pp. 90-96 (2002).

(Continued)

*Primary Examiner* — Michael G Hartley
*Assistant Examiner* — Nabila Ebrahim
(74) *Attorney, Agent, or Firm* — Patton Boggs LLP

(57) ABSTRACT

A combination of chemical agents reduces reductive stress by limiting the accumulation of high-energy electrons potentially available to the electron transport chain. A method of metabolic uncoupling therapy comprises: analyzing a specific physiologic process involving reductive stress; identifying a plurality of MUT agents that modulate metabolic pathways by influencing electron flux; and formulating a combination of MUT agents that limits the accumulation of high-energy electrons potentially available to the electron transport chain.

1 Claim, No Drawings

OTHER PUBLICATIONS

Tarnopolsky MA, Beal MF. Potential for creatine and other therapies targeting cellular energy dysfunction in neurological disorders. Ann Neurol. May 2001; 49(5): 561-74.

Weger et al.; "Incomplete Renal Tubular Acidosis in primary osteoporosis"; Osteoporosis, International; vol. 10; pp. 325-329 (1999).

* cited by examiner

METABOLIC UNCOUPLING THERAPY

CROSS-REFERENCE TO RELATED APPLICATIONS

This application is a divisional of U.S. patent application Ser. No. 11/703,446 filed Feb. 6, 2007, which is a divisional of U.S. patent application Ser. No. 10/462,958 filed on Jun. 17, 2003, which is a continuation-in-part under 37 CFR 1.53(b) of U.S. patent application Ser. No. 09/749,584 filed on Dec. 28, 2000, now U.S. Pat. No. 6,579,866, which issued Jun. 17, 2003. All of the above patent applications are hereby incorporated by reference to the same extent as though fully contained herein.

FIELD OF THE INVENTION

This invention relates in general to novel concepts involving the metabolism of high-energy electrons in animals, and more particularly to their physiological effects in mammals.

BACKGROUND OF THE INVENTION

There is currently an epidemic of lifestyle related health disorders. These include, but are not limited to, high blood pressure, diabetes, dyslipidemia, hyperlipidemia, hypercholesterolemia, insulin resistance, inflammation, vascular disease, heart disease, stroke, overweight, obesity, neuronal and/or cognitive dysfunction, dementia, attention and attention/hyperactivity disorders, mood disorders, muscular damage, muscular deterioration or soreness, athletic compromise, sarcopenia, glucose intolerance and other disorders of glucose metabolism, premature aging, skin deterioration and/or damage either associated with, or not associated with, sun exposure, loss of muscle tone, frailty, and bone loss.

Many of these disorders may be understood by analysis of the forces that shaped the evolution of mankind. This analysis provides insight into the interactions between the current environment and the human genome.

Genetic adaptations proceed on a scale measured in hundreds of thousands of years. In contrast, current environmental and dietary changes occur in a much-accelerated fashion. Our "stone age" genes are a poor match for the demands placed upon them by our current lifestyles. This dys-synchrony is manifestly responsible for the predisposition to, and development of, chronic disease.

Multiple factors form the mechanistic basis for the adverse biological processes responsible for the development of chronic disease and many other health problems. An understanding of these factors is important in the fashioning of a meaningful treatment approach. The multiple biological processes, and the resulting forces exerted by them in an organism, have evolved over millions of years and form the basis for the current intricate biological actions and reactions that occur at the cellular level. Each metabolic pathway consists of many small, carefully orchestrated steps that modulate, and in turn are influenced by, many of the chemical pathways within each cell. The most fundamental cellular processes are involved. Subtle effects are magnified many fold at each step of every pathway until ripples are felt in the far reaches of the cell. A perturbation in a metabolic pathway that produces changes exceeding the normal ranges developed through evolution forces may ultimately derail the delicate chemical balance that forms the basis for cellular homeostasis. When this happens, cells, tissues, organs, and even organisms manifest various disease processes.

The evolutionary history responsible for the current metabolic processes in organisms tells an interesting story. The most fundamental property of all living organisms involves the ability to extract and harness energy from their surroundings. This energy is used to drive thermodynamically unfavorable processes involving the generation of cellular order and complexity. They form the basis for cellular functions. These include growth, repair, and reproduction.

In the evolutionary development of living organisms, apparently the safest and most efficient mechanism for cellular energy transduction involved the directed flow of high-energy electrons down an energy ladder in multiple small steps. Each downward step involved the transfer of an electron from one state to another, slightly lower in energy. This was associated with the release of a packet of energy in a biologically acceptable manner, which could be captured and saved for future use. These processes were present in the earliest formulations of photosynthesis and metabolism. They constituted the earliest design of an electron transport chain (ETC). These processes were in place before oxygenic photosynthesis evolved, thus predating the oxidizing atmosphere that dominates the earth today.

Weak electron acceptors such as hydrogen sulfide, organic acids, and nitrate were initially utilized. This only allowed generation of meager amounts of energy. Nevertheless, when atmospheric oxygen became available in high concentration, it became the preferred electron acceptor because it allowed for much more energy generation from fuel sources and had very distinct survival value. Life's transition to an oxygen-rich atmosphere two billion years ago allowed for the unprecedented generation of cellular energy. This benefit was accompanied by the problems of coping with the corrosive and reactive oxygen molecule. The evolutionary events over the past two billion years provided for the development of a modern compromise between the need for a highly efficient oxidative phophorylation process and the need to safely handle the damaging and aging effects of reactive oxygen species (ROS).

The ETC resides on the inner mitochondrial membrane. High-energy electrons flow down an energy gradient while protons are pumped across the mitochondrial membrane. Adenosine triphosphate (ATP) is generated as the protons are transported back across the mitochondrial membrane into the mitochondrial matrix region. For maximal energy (i.e., ATP) production, efficient coupling must exist between the reentry of the protons and ATP generation. In recent years, it has been demonstrated that a finite cellular-membrane proton-conductance exists that is not coupled with ATP generation. This process has been observed to dissipate 20% to 25% of the basal metabolic rate. This is a surprisingly high level of ETC inefficiency that has been preserved over the eons. Because of its high metabolic cost, it must logically provide an extraordinary benefit for the survival of the cell.

Cells have developed powerful anti-oxidant defenses to protect themselves against damage from reactive oxygen species, ROS, which typically comprise free oxygen radicals. Attention in the field has been devoted exclusively to these anti-oxidants. Their function is to spring into action after a free radical is generated and to inactivate or quench it. Even though prevention rather than cure is a more logical way to decrease oxidative damage, no attention has been paid to processes that are critical in the production or generation of ROS. Evidence that forces regulating ROS-production, rather than ex post facto quenching of free radicals, are important and are related to the production of disease; and aging includes the observation that ROS-production is higher in mitochondria from animals with shorter maximal lifespan.

BRIEF SUMMARY OF THE INVENTION

Metabolic uncoupling therapy (MUT) in accordance with the present invention treat the conditions discussed above by providing methods and compositions that limits the accumulation of high-energy electrons potentially available to the electron transport chain.

Various treatments in accordance with the present invention provide enhanced health benefits also by utilizing numerous synergistic mechanisms that together tend to reduce generation of ROS, reduce the PMF, and improve cellular redox status, based upon novel techniques described herein.

Analysis of the mechanistic development of chronic diseases and health disorders, in accordance with the invention, enables the appropriate selection of MUT agents to make novel therapeutic formulations.

Formulations of various combinations of MUT agents in accordance with the invention influence, modulate or control the size of the pool of high-energy electrons, their flux through the ETC, and the generation or dissipation of mitochondrial PMF. Furthermore, formulations in accordance with the invention influence, modulate, or control secondary actions involving metabolic intermediates, components of cellular signaling pathways and subsequent effects upon iron metabolism within the cell. These therapeutic interventions include, but are not limited to: the ability to markedly reduce both de novo as well as secondary generation of free radicals; and the ability to modulate intracellular nucleotide levels, ratios, and turnover with subsequent beneficial effects upon various cell-signaling and other metabolic pathways. These cell-signaling and other metabolic pathways include those for protein kinase C (PKC), diacylglycerol (DAG), the hormone insulin, and those pathways mediating lipid synthesis. Therapeutic interventions in accordance with the invention further include the ability to modulate transitional-metal metabolism, especially copper- and iron-mediated processes related to free-radical biology, and the ability to beneficially influence transcription factors, including AP-1 and NFKB, which play key roles in inflammation and inflammatory processes.

The proton-motive force (PMF) is generated by the pumping of protons across the mitochondrial membrane out of the mitochondrial matrix into the inter-membranous space outside the cell. It is coupled with passage of high-energy electrons down the ETC. The potential energy generated by this separation of charge drives the production of ATP, which is coupled with proton passage back across the inner mitochondrial membrane into the matrix. This process collapses the PMF. The generation of reactive oxygen species is strongly dependent upon the magnitude of the PMF. Consumption of the PMF diminishes the concentration and half-life of semiquinone moieties along the ETC. This reduces the rate of generation of reactive oxygen species, ROS. By collapsing the PMF, MPC serves to uncouple proton pumping from ATP-production. This lowers the generation of ROS. In the prior art, this insight suggested a key role for mitochondrial proton conductance (MPC). The uncoupling of proton pumping from the metabolism of ATP production formed a basis for regulating ROS in the prior art. In contrast, a primary function of MUT agents and MUT formulations in accordance with the present invention is to limit the accumulation of high-energy electrons potentially available to the electron transport chain.

A methodology of metabolic uncoupling therapy in accordance with the invention comprises: analyzing a specific physiologic process, including delineating the metabolic pathways related to reductive stress; identifying a plurality of MUT agents that modulate the metabolic pathways by influencing electron flux; and formulating a combination of MUT agents that limits the accumulation of high-energy electrons potentially available to the electron transport chain.

Further, a method preferably includes selection of MUT agents based on their interactions with each other to maximize synergy of the agents. In another aspect, a method includes combining specific amounts and ratios of a plurality of agents in a MUT formulation for administration in a prescribed manner for a prescribed period of time. Embodiments in accordance with the invention comprise compositions of chemical compounds, MUT agents, that are useful in metabolic uncoupling therapy. Selected chemical compounds, chemical species, dietary and pharmaceutical supplements and other nutritional agents (collectively "agents") in specified amounts, prescribed ratios, and synergistic combinations are scientifically selected to act at one or multiple focal metabolic locations to maximize the desired beneficial results, while simultaneously minimizing undesired side effects.

Abnormalities in flux of high-energy electrons, their subsequent metabolic effects, and induced signaling alterations play pivotal roles in the delicate balance between health and disease. A method and a composition in accordance with the invention provide metabolic intervention designed to achieve beneficial modulation of such processes. Embodiments in accordance with the invention treat, improve, and/or normalize various aberrant metabolic pathways central to the development and progression of numerous diseases including, but not limited to those named above. Metabolic uncoupling therapy in accordance with the invention has far reaching beneficial effects on inflammation, glucose and insulin metabolism, mitochondrial function, muscle preservation and hypertrophy, athletic performance, post-exercise skeletal muscle recovery, hemostasis and thrombosis, development of functional foods, skin care, vascular disease, neural and cognitive decline, and bone metabolism, as well as cell, organ, and tissue preservation.

MUT in accordance with the invention includes, among other effects, manipulation of flux of high-energy electrons through biochemical pathways; modulation of related cell processes and signaling systems; modulation of metabolic intermediates involved in the production of high-energy electrons (such as semiquinone moieties); and modulation of nucleotides, nucleotide ratios, and nucleotide cycling.

MUT agents in accordance with the invention act in various specific combinations, compositions, amounts, and ratios to maximize beneficial effects. Further, MUT in accordance with the invention minimizes adverse side effects that might otherwise occur through inappropriate usage of various compounds and compositions not in accordance with the invention. Because of these beneficial effects, MUT may be utilized for the prevention of a multitude of conditions, in addition to its use as a therapeutic modality under conditions of disease and aging.

DETAILED DESCRIPTION OF THE INVENTION

Every animal cell requires regulation of fundamental metabolic processes and properties. Cell regulation includes regulating the control, generation, concentration, half-life, energy levels, flux, and recycling of high-energy electrons, as well as the cellular processes that high-energy electrons influence, such as nucleotide concentrations, ratios, and redox state. The instantaneous metabolism of high-energy electrons not only reflects the results of a number of cellular biochemical reactions, but also directly relates to and regulates cellular phosphorylation and redox status. Abnormalities in these pathways are typically directly implicated in disease causation. Powerful modulation of these parameters thus is implicitly involved in disease treatment.

A beneficial intervention of MUT in accordance with the invention typically modulates electron flux and related pathways. MUT provides a holistic, multi-modality approach utilizing one or more formulations designed for the treatment of specific and general disease processes. In another aspect, MUT provides a method of devising a specific formulation, or combination, of ingredients including MUT agents, and a specific program of dosage designed for a particular individual at a particular time in a disease process manifesting in a specific way. Other applications include provision of MUT for various preventative applications.

MUT agents include, but are not limited to, seven groups of agents described herein. Each group comprises agents sharing a similar functional attribute that beneficially modulates one or more biochemical pathways. This allows the combination of various agents chosen from different groups that act synergistically in a desired manner. In contrast, the prior art has not recognized the existence of or formulated distinct groups of agents, each group with different mechanisms of action, functionality, and synergistic options.

Each group is defined by a set of functional attributes. Every agent in each group shares the functionalities of that group. On the other hand, each member of a specific group has a separate, distinct chemical composition. This imbues each agent within a specific group with biochemical properties that differentiate it from other agents in that group. The in-common and the distinct properties of various MUT agents, their association with a specific situation being addressed, the desired result which is to be achieved, and the metabolic interactions between various agents when used in certain amounts, combinations and ratios, and differing clinical considerations dictate the selection of MUT agents from various groups, and their amounts and relative weight ratios. The formulation and dosage of MUT agents depend in part upon the clinical knowledge of one skilled in the art. For example, pharmacologic interactions between agents under certain biological conditions are sometimes evaluated by one skilled in the art to determine choices of agents (including amounts, combinations, and ratios) for MUT.

In contrast, in the prior art, certain compositions of chemical compounds were formulated rather simplistically. One, two, or several species were chosen to achieve a desired result. The general thought process involved the combination of individual chemical compounds, each of which had been previously shown to have some desired beneficial impact. Generally, it was believed that if a little was good, more of each agent was better. This led to extensive dose-related toxicity, which required backing down the individual doses and was accompanied by a decrement in beneficial action. Since the motivation behind specific agent choices was rarely driven by any basic etio-pathogenic mechanistic understanding at the molecular or sub-cellular level, synergies were not apparent, were not recognized, and were not incorporated into the overt decision-making process for any formulation. This precluded taking full advantage of existing, but unrecognized, synergistic interactions.

One benefit of MUT in accordance with the invention is therapeutic efficacy with minimized dose-related toxicity. Another benefit of enhanced therapeutic efficacy realized in accordance with the invention involves enhancement of physiologic effect to maximize metabolic action by customizing the choice of MUT agents to produce a certain specified result in a desired cellular location. This is possible by selecting agents whose individualized chemical properties allow them to localize at a specific location in the cell. For example, certain agents may localize to biological membranes due to their lipophilic properties, others may be both water and lipid soluble, thus allowing them to cross the cell membrane and build up in the cytosol, while others may specifically localize in the endoplasmic reticulum or the mitochondrial space. The higher "local" concentration thus produced may facilitate biological activity without the development of systemic toxicity. Additional possible benefits of this type of "targeted" approach allow more effective utilization of multiple potential beneficial attributes of a specific compound. For example, an agent that localizes to the mitochondrial space has therapeutic effects upon electron flux at this site. If it also has known beneficial effects upon calcium metabolism, it may have synergistic actions upon mitochondrial calcium metabolism due to its higher local concentration and multiple beneficial attributes. The beneficial synergies generated include a higher "local" concentration at a desired location, more biological activity with less systemic toxicity, and improvement in a related physiologic process (e.g., calcium handling).

Each group of agents shares a common intra-group functionality which defines the group. The groups as a whole, in addition, share beneficial inter-group synergy that contributes to the utility of the invention. This includes the beneficial regulation and modulation of high-energy electrons. It may be conceptualized as multiple groups forming an interactive network designed to maximize the metabolic effect by utilizing cross-talk and interaction within as well as between groups. The overt benefit of the knowledge of the existence of these discrete functional categories is the flexibility in formulating therapeutic compositions with better clinical "fit", enhanced efficacy, improved safety profile and broader applicability. An example involves the potentially deleterious effects of excessive reducing power in a cell or tissue. Reducing power is ameliorated in accordance with the invention by decreasing the production of high-energy electrons. It is also improved by increasing the rate of removal of high-energy electrons as well as by the metabolic "discounting" of the energetic status of individual electrons (i.e., the metabolism of NADH to $FADH_2$). A preferred embodiment in accordance with the invention may combine several or all possible approaches.

A molecular understanding of the metabolic processes and the powerful therapeutic synergy of the different functional groups provide additional insight including, but not limited to, actions affecting metabolic modulation. The metabolic modulation is achieved by mechanisms such as diversion to futile cycles, thermogenic electron shuttles, sacrificial consumption, and bio-neutralization. It may also utilize transcriptional, post-transcriptional, allosteric, substrate-driven, enzymatic, non-enzymatic, cyclic, and linear processes.

A heightened safety profile associated with embodiments in accordance with the invention includes preventative formulations. Once a disorder has developed, it already has adverse implications. This justifies the use of potentially toxic therapeutic interventions. On the other hand, in a purely preventative posture, no adverse condition exists and therefore there is no justification for administration of a potentially toxic regimen. This reasoning forms the basis for expanded applicability of formulations of MUT agents.

The prior art failed to evaluate the evolutionary history that was responsible for many of today's health woes. With such an evolutionary perspective, it is possible to understand why many of the current health issues arise. Many health problems result from the poor adaptation of our genes (driven by evolutionary forces) to our current diet and lifestyle choices. The gene pool that survived the brunt of evolutionary pressure was forced to make decisions representing a critical compromise. They were forced to balance the generation of abundant cellular energy with the safe handling of the corrosive oxygen molecule. The implications of this evolutionary choice plague us today. They also provide prescient insight that facilitates the formation of a beneficial metabolic uncoupling therapy in accordance with the invention.

Numerous factors contribute to the selection of MUT agents, as well as their specific amounts and ratios in a desired formulation. These include, for example, the mechanism driving a specific metabolic pathway, other possible related pathways, and the clinical setting. For example, if one pathway is substrate-driven, then a particular amount of a particular agent is preferred. If an associated pathway is enzymatically regulated and the active agent acts via an allosteric mechanism, then a much smaller amount is preferred. If administration of one agent has an indirect effect of enhancing the bio-availability of another agent, this impacts both the absolute levels of each of the agents as well as their respective weight ratio. This knowledge, combined with the need for a specific desired result in a specific clinical setting, is typically utilized by one skilled in the art to direct the construction of a precise formulation designed for a specific clinical condition.

A central feature of the invention is the use of seven different functional groups of active agents. It is understood that other agents not named are also useful in methods and chemical compositions in accordance with the invention. The seven functional groups are enumerated and defined below.

Group 1 is characterized by small electrophilic biomolecules. These include TMG (Trimethylglycine), choline, phosphatidyl choline, SAMe (S-adenosyl methionine), carnitine, ALC (acetyl L-carnitine), propionyl carnitine, myo-inositol, sphingomyelin, glycerylphosphorylcholine, and acetylcholine.

Each of these molecules differs in its respective chemical structure and recognized functions. They do, however, contain a common chemical moiety. They have a positively charged nitrogen (N) or sulfur (S) atom in their structure, rendering an adjacent methyl group electron deficient. They react with electron donors in an irreversible reaction by the transfer of a pair of electrons to the electron-deficient methyl group, thus splitting this group from the positive N or S moiety. No toxic products are generated by this chemical reaction. This reaction transforms the electron donor into a more oxidized form (i.e., NADH is transformed into NAD+). In this example, the nucleophilic hydride ion from NADH is transferred to the electron deficient methyl group of the biomolecule. This is followed by the splitting off of the methyl group and the formation of methane associated with the oxidation of NADH to NAD+. Since the reaction consumes the biomolecule in the reaction, a continuous supply is required to maintain the effect.

The presence of an electrophilic N or S moiety within each agent in this group forms the chemical basis that defines the common functionality of the group. The remaining chemical components of each agent are otherwise quite variable. This invests them with additional, disparate chemical qualities that may be beneficially utilized in the invention. For example, choline and phosphatidyl choline (PC) are both in Group 1, yet PC has a long phosphatidyl group attached to the choline group. This chemical difference defines additional functional differences that influence the relative applicability of each agent to any specific situation. The chemical and functional differences may also be important in the determination of specific amounts of an agent used and its weight ratio with other agents. In this example, PC tends to localize to membranes, play key roles in intra-cellular signaling pathways, and impact the function of protein receptors in the membrane. Choline, while possibly affecting membrane metabolism and physiology, plays a more specific role in neurotransmission. Thus, these types of chemical and functional differences between MUT agents play key roles in the choices of amounts, types, and ratios of agents.

Another type of interaction that is important involves the effect of one agent upon the bioavailability of another agent. For example, choline improves the bioavailability of carnitine. If this is the only reason for utilizing choline, a specific dose may be chosen in a straightforward manner. If, however, carnitine bioavailability, as well as neurotransmission concerns, needs to be addressed, this impacts dosing and agent ratio choices. If the specific electron-modulating action of choline is also necessary, then greater amounts of choline are typically chosen, because in these reactions choline is consumed and is not regenerated.

Considerations regarding the location of beneficial action (e.g., which organs are involved—liver or brain; which cells are involved; which intra-cellular location) also affect the intra-group choice of agents. For example, some agents are not able to cross the blood-brain barrier very efficiently. This suggests increasing the dosage or using another agent to facilitate brain uptake. Thus, embodiments in accordance with the invention contain selected Group 1 agents, amounts, and ratios to maximize therapeutic benefit.

Group 2 agents are characterized by anti-consumptive methyl agents, including creatine and folic acid. These agents provide a continuous supply of methyl groups that help replace methyl groups lost by other agents while performing their prescribed role. For example, Group 1 agents are typically consumed, and not regenerated, as they are utilized in the invention. A Group 2 agent provides replacement for the ongoing loss of methyl groups from, for example, the Group 1 reactions.

Group 3 agents are characterized by biological macromolecules, including DHA (docosahexanoic acid), EPA (eicosapentanoic acid), and albumin. These are molecules that by their size, configuration, numbers of disulfide bonds, or a combination of these features undergo chemical reduction. That is, they are electron acceptors, sometimes at one molecular location, but typically at multiple separate locations in each of the molecules. These reactions are either reversible or irreversible. When irreversible, then once all the sites available for acceptance of electrons are consumed, they are removed and biologically recycled. In this sense, they are large, sacrificial, anti-reductive biological compounds. DHA and EPA are both long-chain fatty acids. Albumin is a protein. These structural differences make them useful in different locations. Albumin is primarily a plasma protein, and the fatty acids are usually found in cellular biomembranes. DHA has more pronounced structural utility, and EPA is involved in cellular signal-transduction pathways. The fatty acids have different numbers of double bonds, which also affect their chemical reactivity. EPA modulates membrane phospholipase activity and membrane turnover. Agent composition, amounts and ratios also depend upon such factors as the clinical condition being treated, the degree of inflammation present, and the omega-6/omega-3 ratio, as well as absolute levels of omega-6 and omega-3.

Group 4 agents are characterized as oxaloacetate (OAA) precursors, including PYR (Pyruvate), ASP (Aspartate), GLY (Glycine), and SER (Serine). These are all small amino or alpha-keto acids, which are biochemical precursors of oxaloacetate via differing pathways and under different metabolic conditions. This is significant because of the ability of OAA to function as an electron-acceptor in association with the oxidation of NADH to NAD+. Depending upon the prevailing chemical environment in the cell, one agent may be selected over others due to its preferred metabolism to OAA. Other factors useful in the determination of one of these agents over another also involve other metabolic pathways they modulate or in which they react. These are different from agent to agent and involve considerations involving energy generation, protein synthesis, neurotransmission, and phospholipid synthesis, and may also include electron-shuttle function. Some of the functions of Group 4 agents involve allosteric modulation of enzymes, substrate-driven reactions, cyclic pathways or post-transcriptional modification. The selected function of a Group 4 agent in any specific circumstance is influenced by the clinical situation and the desired result. Together these considerations guide the specific choices regarding combinations of agents, amounts and ratios.

Group 5 agents are characterized by B vitamins and structurally related entities, including folate, riboflavin, B1, B3, niacinamide, nicotinamide, polynicotinate, B6, B12, biotin, pantothenic acid, and other related chemical species. These compounds comprise the B-vitamin group and include pyrimidine, pyrazine, and other aromatic rings. They are able to undergo reductive addition reactions. Selection of one entity over another is determined in part by other B vitamin properties, (e.g., the enzyme for which it acts as a co-factor, location of the enzyme, effects upon cyclic GMP and other separate biochemical profiles). Selection of Group 5 agents is also influenced by the close functional association among B vitamins and their own internal synergy.

Group 6 agents are characterized by electron cycling agents, including coenzyme Q10, lipoic acid, and acetoacetate. These compounds are easily cycled by accepting and then releasing electrons. This process modulates the NADH redox state, alters other biochemical characteristics of each agent, and forms a cyclic rather than linear biochemical pathway. In addition to their shared electron-cycling properties, they each have different chemical traits manifested under differing conditions. These factors help direct agent choices from this group. Coenzyme Q10 is found primarily within membranes, and is frequently associated with the electron transport chain along the inner portion of the inner mitochondrial membrane. It also has anti-oxidant functionality. Lipoic acid is both water and lipid soluble and has access to most biological compartments. Also, by being a cofactor for enzymes, it plays a central role in energy generation and mechanisms of glucose and insulin metabolism. Lipoic acid is able to bind transition metals, thereby modulating their role in numerous important physiological reactions. Acetoacetate is a ketone body used as a fuel source and a precursor of neurotransmitters, and it has access to the brain compartment.

Group 7 agents are characterized by iron-binding agents, such as polyphenolic agents and desferoximine. The reduction of ferric to ferrous ion facilitates the release of an iron atom from protein-binding agents (e.g., ferritin). This causes the iron transition metal to act catalytically by facilitating the generation of electrons, which contribute to the production of ROS and subsequent tissue damage. This damage involves disruption of DNA, lipid structures, and proteins. Group 7 agents have the ability to bind and inactivate free iron. This forms the basis for their beneficial actions. Polyphenolic compounds also are powerful anti-oxidants, modulate many intra-cellular signaling pathways, and protect lipoproteins from oxidative stress. Preferably, these additional properties are considered in the selection of Group 7 agents.

Therapeutic combinations of MUT agents are formulated in accordance with the invention by selection of:

two or more agents from Group 1;
one or more agents from Group 4;
two or more agents from Group 5; and
one or more agents from Group 6.

Certain embodiments in accordance with the invention also include one or more MUT agents from Groups 2, 3, and 7.

Listed below are exemplary MUT agents and dosage ranges used in molecular uncoupling therapy in accordance with the invention. In preferred embodiments, a plurality of MUT agents are used in combination.

| MUT Agent | Daily Dose Range | Daily Dose Preferred |
| --- | --- | --- |
| Creatine | 10 mg to 30 g | 1 g to 10 g |
| Acetylcholine | 1 mg to 1 g | 10 mg to 500 mg |
| Propionyl L-carnitine | 1 mg to 10 g | 20 mg to 2 g |
| Myo-inositol | 10 mg to 10 g | 100 mg to 2 g |
| Pyruvate (Pyruvic acid) | 50 mg to 30 g | 500 mg to 20 g |
| Aspartate (Aspartic acid) | 50 mg to 30 g | 500 mg to 20 g |
| Serine | 50 mg to 30 g | 500 mg to 20 g |
| Glycine | 50 mg to 30 g | 500 mg to 20 g |
| Coenzyme Q10 | 1 mg to 2,000 mg | 10 mg to 800 mg |
| Alpha Lipoic Acid (Lipoic acid, r lipoic acid, r alpha lipoic acid, racemic mixture) | 1 mg to 4,000 mg | 10 mg to 1,400 mg |
| Eicosapentanoic Acid (EPA) | 10 mg to 4,000 mg | 50 mg to 2,000 mg |
| Docosahexanoic Acid (DHA) | 10 mg to 4,000 mg | 50 mg to 2,000 mg |
| Trimethylglycine (TMG) | 100 mg to 5,000 mg | 500 mg to 3,000 mg |
| Dimethylglycine (DMG) | 100 mg to 5,000 mg | 500 mg to 3,000 mg |
| Choline | 25 mg to 6,000 mg | 100 mg to 2,000 mg |
| Phosphatidyl Choline | 25 mg to 20 g | 500 mg to 5 g |
| SAMe | 10 mg to 3,000 mg | 100 mg to 1,600 mg |
| Folic Acid (folate) | 100 mcg to 20 mg | 400 mcg to 10 mg |
| Riboflavin | 1 mg to 100 mg | 5 mg to 30 mg |
| B1 | 1 mg to 400 mg | 10 mg to 100 mg |
| B3 | 1 mg to 4,000 mg | 10 mg to 2,000 mg |
| B6 or pyridoxine (pyridoxyl phosphate) | 1 mg to 400 mg | 10 mg to 200 mg |
| B12 | 10 mcg to 1,000 mcg | 20 mcg to 500 mcg |
| Biotin | 10 mcg to 20 mg | 300 mcg to 12 mg |
| Pantothenic Acid (pantothenate) | 1 mg to 1,000 mg | 10 mg to 250 mg |
| Carnitine | 5 mg to 20 g | 20 mg to 10 g |
| Acetyl L-carnitine | 1 mg to 10 g | 20 mg to 10 g |
| Polyphenolic anti-oxidants | 1 mg to 2 g | 20 mg to 1 g |
| Sphingomyelin | 5 mg to 5 g | 20 mg to 2 g |
| Glyceryl phosphoryl choline | 5 mg to 6 g | 20 mg to 4 g |
| Magnesium-creatine | 10 mg to 50 g | 50 mg to 20 g |
| Albumin | 10 mg to 100 g | 20 mg to 50 g |
| Acetoacetate | 10 mg to 300 g | 50 mg to 100 g |

Listed below are exemplary MUT agents and corresponding agent ratios in accordance with the invention.

| Agent Ratios | Range |
| --- | --- |
| Creatine/TMG | 1/20 to 30/1 |
| Creatine/Carnitine | 1/10 to 250/1 |
| Creatine/Pyruvate | 1/20 to 25/1 |
| Creatine/Aspartate | 1/10 to 25/1 |

Many of the agents listed may occur in long polyene chain form. These are also to be included in the invention. Such formulations may include, for example, poly(ene) phosphatidyl choline.

In general, referral to a specific agent is to be understood as referring to all forms of that agent. For example, the terms niacin, niacinamide, nicotinamide, and polynicotinate are essentially synonymous. Similarly, the term "alpha lipoic acid" (ALA) refers to lipoic acid, thiotic acid, R alpha lipoic acid, and racemic mixtures thereof.

An imbalance in the pool of high-energy electrons induces abnormalities in numerous pathways of cellular metabolism and plays a key role in the development of pathologic states. One common abnormality of cellular metabolism involves development of reductive stress, that is, increased electron pressure from too many high-energy electrons. Reductive stress impacts intracellular signaling systems that are causally related to metabolic health problems.

Intracellular accumulation of triglyceride (TG) occurs early in numerous diseases. Accumulation of TG is clearly a risk factor for the subsequent development of obesity and the associated abnormalities of glucose and insulin metabolism. TG content has been correlated with intracellular long chain fatty acyl CoA (LCAcCoA) content. Accumulation of LCAc-CoA is suspected to increase production of diacylglycerol (DAG), a potent stimulator of Protein Kinase C (PKC) isoenzymes. Certain PKC activity inhibits the intracellular insulin-signaling pathway and impairs insulin-stimulated glucose transport; that is, it causes the development of insulin resistance, the cornerstone involved in the etiology of a host of metabolic diseases present today in epidemic proportions. Intracellular TG buildup is treatable by MUT in accordance with the invention.

Alterations in cellular redox status modulate a number of important intracellular metabolic processes. At any point in time, each cell resides in a particular redox state. Redox states fall along a continuum of values. Intracellular nucleotide ratios determine where along this continuum each cell resides at any particular instant. Most cells generally tend to function in a relatively reduced biochemical state. When the cell becomes even more biochemically reduced, it moves in the direction of reductive stress. Reductive stress may be defined as an abnormally increased electron pressure or "reducing power". It typically occurs either as a result of pathological processes leading to an excess of high-energy electrons, or a failure of mechanisms available for dealing with this rise in electron pressure, or both. It was recognized by the inventor that reductive stress is not only more common than oxidative stress, but it is also the main source of production of reactive oxygen species ("ROS") and reactive nitrogen species ("RNS") in the body.

A beneficial effect of substances containing reducible groups, which relieve this electron pressure, defines a category of anti-reductants. The in vivo action of compounds capable of oxidizing NADH to NAD+ is analogous to the in vitro action of electron acceptors such as methylene blue.

Abnormalities in the functioning of the Krebs cycle and the electron transport chain are attributable to reductive stress. In this context, it is important to realize that stress induced by reductive conditions or a diet deficient in anti-reductive components causes identical pathological states. For example, ethanol-induced reductive stress in liver, or a diet deficient in electrophilic groups, produces the same disorders. Regardless of its cause, reductive stress leads to undesirable accumulation or generation of reactive oxygen species (ROS), to hypomethylation of DNA, and to impaired oxidation of triglyceride (TG).

Vasodilation and increased blood flow are the earliest vascular changes associated with diabetes and also with acute hyperglycemia in non-diabetic humans. These changes are associated with an increase in the NADH/NAD+ ratio. Increased glycolysis is associated with an increased cytosolic NADH/NAD+ ratio. The mechanism behind the association of augmented glycolysis and elevation of the NADH/NAD+ ratio appears to result from a dys-equilibrium between the rate of oxidation of glyceraldehyde 3-phosphate ("GAP") to 1,3 diphosphoglycerate ("1,3 DPG"), which is associated with the reduction of NAD+ to NADH, and the rate of reduction of pyruvate to lactate (coupled with the oxidation of NADH to NAD+).

Metabolic consequences of an increase in the cytosolic ratio NADH/NAD+ impact the activity of numerous cytoplasmic and mitochondrial enzymes that utilize NADH and NAD+ as cofactors and/or are regulated by them. This is associated with several disorders of lipid metabolism. These include increased de novo synthesis of DAG and subsequent activation of PKC. These alterations have been linked to many metabolic and functional vascular and neural changes. Inhibition of fatty-acid oxidation and increased lipogenesis are associated with an increase in mitochondrial NADH/NAD+ ratio.

Elevation of the cytosolic NADH/NAD+ ratio is associated with intracellular increases in glycolytic triose phosphate compounds, which cause increases in DAG with subsequent activation of PKC isoforms. These PKC isoforms lead to the development of insulin resistance and produce detrimental effects upon the insulin-signaling pathway.

In accordance with the invention, alteration of NADH levels or modulation of the NADH/NAD+ ratio occurs by supplementation with various anti-reductive compounds in Groups 1 through 6. This tends to oxidize NADH to NAD+, thus lowering the NADH/NAD+ ratio, which produces a fall in lipogenesis and has a deactivating effect upon PKC.

A more oxidized NADH/NAD+ ratio also tends to down-regulate the NADH oxidase system and tends to keep coenzyme Q10, an electron acceptor, in a relatively more oxidized state. Both of these mechanisms potently down-regulate production of harmful ROS and RNS.

Example 1

An exemplary embodiment in accordance with the invention suitable for metabolic uncoupling therapy of hepatic steatosis/steatohepatitis was formulated. Daily administration of a composition containing the following ingredients is recommended for a period of time necessary to achieve a desired result, typically for a time period in a range of from two months to twelve months, or until resolution of the hepatic fat accumulation and/or inflammation. Two doses to three doses per day are used. One composite daily dose contains:

| | |
|---|---|
| Coenzyme Q10 | 100 mg |
| R alpha lipoic acid | 300 mg |
| Eicosapentanoic acid (EPA) | 1 g |
| Trimethylglycine | 500 mg |
| Phosphatidyl choline | 3 g |
| S-adenosyl methionine (SAMe) | 200 mg |
| Carnitine | 500 mg |
| Aspartic acid | 2 g |
| Vitamin B1 | 25 mg |
| Vitamin B2 | 25 mg |
| Vitamin B3 | 25 mg |
| Vitamin B5 | 25 mg |
| Vitamin B6 | 25 mg |
| Folic acid | 800 mcg |

A dose may also include:

| | |
|---|---|
| Biotin | 1 mg |
| Hydroxycitric acid | 500 mg |
| Vitamin B12 | 1 mg |

The clinical condition hepatic steatosis/steatohepatitis, as well as the primary and secondary chemical actions and physiologic functionalities of each of the available agents, were considered in selecting agent composition, amounts and ratios. EPA is a beneficial MUT agent for therapy of hepatic steatosis/steatohepatitis, but also facilitates fat burning by other actions that include the inhibition of acetyl CoA carboxylase (ACC) and the activation of carnitine palmitoyl transferase (CPT). Increased fat burning, especially in the liver, lowers the intracellular hepatocyte fat content and ameliorates the condition. Coenzyme Q10, in addition to modulating electron flux, acts as a potent anti-oxidant with anti-inflammatory actions. It also improves activity of the electron transport chain, thus up-regulating reverse electron transport. This discounts the energy status of electrons, further speeding up fat burning as well as oxidizing the Q-couple. This decreases the generation of oxidative stress, thereby indirectly down-regulating the hepatic inflammatory process. Aspartate, another MUT redox-active agent, additionally increases hepatic fat burning by up-regulating futile, thermogenic carbohydrate cycles, which decreases the intra-cellular fat burden. This further down-regulates the inflammation typically present under these conditions. Carnitine, a Group 1 agent, also is used as a cofactor for the transport of activated long-chain fatty acids into the mitochondria where they undergo complete oxidation. B vitamins, Group 5 agents, in addition to their primary actions as described above, are useful cofactors for many of the enzymatic pathways involved in the overall therapeutic process. These numerous individual modulations act synergistically to maximize hepatic fat burning, further down-regulating hepatic fat stores and associated inflammation.

The selection of the MUT agents of Example 1 exemplifies how methodical selection of agents facilitates the synergy deriving from the combined activity of the primary (related to handling of high-energy electrons) and secondary (synergistic actions unrelated to the primary effects) actions of the MUT agents. By combining the metabolic uncoupling therapy agents into a formulation that merges the effects with the other additional, implicit, synergistic, beneficial functions of the specifically chosen agents, the functionality of the formulation is maximized.

Prior art formulas sometimes included individual isolated agents similar to a MUT agent, or combinations of agents, known in the prior art to improve specific global clinical endpoints, such as hepatic fat content. Nevertheless, because the prior art failed to consider the detailed molecular mechanisms involved, including the primary and secondary interactions at the cellular level, the prior art did not anticipate the additional beneficial secondary actions of MUT in accordance with the invention. Such benefits of MUT result from novel considerations of metabolic molecular actions which are not otherwise apparent. The prior art did not recognize or teach the molecular synergies described in this specification. These include, but are not limited to, numerous influences of the redox state on metabolic pathways, and the detailed mechanisms available for the therapeutic modulation of the redox state at many levels and many sites. The molecular synergies provided by embodiments in accordance with the invention include the beneficial, functional, molecular interactions characterizing each of the defined Groups 1 through 7, the secondary actions of each agent, including their metabolic interactions with the primary molecular effects of each of the MUT active agents, and the synergy accruing from the inter-group interactions. The selection and application of the interactions, along with the ability to intercede in metabolic pathways and mechanisms in controlled and precise ways, is a benefit of embodiments in accordance with the invention.

Example 2

Another exemplary embodiment in accordance with the invention suitable for metabolic uncoupling therapy of hepatic steatosis/steatohepatitis was formulated. Daily administration of a composition containing the following ingredients is recommended for a period of time necessary to achieve a desired result, typically for two months to twelve months, or until resolution of hepatic fat accumulation and/or inflammation. Two doses to three doses per day are used. As discussed above, certain MUT agents provide synergistic secondary benefits when chosen and combined in specific amounts and ratios designed for indicated uses. Pyruvate and EPA have secondary actions as outlined above. Green tea leaf extract lowers the respiratory quotient (RQ) by beneficially modulating the amount of fat the body burns. It increases fat burning and decreases the content of intracellular fat. It also has anti-inflammatory activity. Pyruvate, in addition to oxidizing NADH to decrease the NADH/NAD+ ratio, also augments fat oxidation and inhibits fat storage. Creatine, in addition to facilitating methyl group availability, also indirectly turns on the enzyme AMP kinase (AMPK), which further augments fat burning (aside from its MUT effects). The choice of multiple B vitamins beneficially modulates MUT activity. They also have beneficial secondary actions mediated via their roles as enzyme cofactors, stress reducers, and anti-inflammatories. One dose contains:

| | |
|---|---|
| Creatine | 2 g |
| R alpha lipoic acid | 200 mg |
| SAMe | 400 mg |
| EPA | 500 mg |
| TMG | 500 mg |
| Green tea leaf extract | 20 mg |
| Pyruvate | 3 g |
| Phosphatidyl choline | 2 g |
| ALC | 500 mg |
| Vitamin B1 | 25 mg |
| Vitamin B2 | 25 mg |
| Vitamin B3 | 25 mg |
| Vitamin B5 | 25 mg |
| Vitamin B6 | 25 mg |
| Folic acid | 800 mcg |

A dose may also include:

| | |
|---|---|
| Conjugated linoleic acid (CLA) | 2 g |

Example 3

An exemplary embodiment in accordance with the invention was formulated for achieving weight loss using metabolic uncoupling therapy (MUT). Two doses to three doses per day are recommended. Additional beneficial attributes are included in this formulation. Fat burning is augmented by utilizing properties in addition to the MUT properties of the agents chosen for this formulation. These include the fact that aspartate increases hepatic fat oxidation utilizing mechanisms described above. Carnitine increases carnitine palmitoyl transferase (CPT) activity. Choline acts to increase carnitine levels. This acts synergistically to increase fat burning. Each dose contains:

| | |
|---|---|
| Aspartic acid | 2 g |
| Biotin | 600 mg |
| HCA | 500 mg |
| Chromium | 400 mcg |
| Carnitine | 25 mg |
| Choline | 500 mg |
| TMG | 200 mg |
| SAMe | 200 mg |
| ALA | 200 mg |
| B1 | 25 mg |
| B2 | 25 mg |
| Folate | 1 mg |
| Niacinamide | 275 mg |
| Creatine | 1 g |

Each dose may include medium chain triglycerides (MCT).

| | |
|---|---|
| MCT | 10 g |

These augment the activation of futile, thermogenic carbohydrate cycles, further adding to the weight loss activity.

Example 4

An exemplary embodiment in accordance with the invention was formulated for treating hyperlipidemia using metabolic uncoupling therapy (MUT). Two doses per day are recommended. Each dose contains:

| | |
|---|---|
| Pyruvate | 2 g |
| Aspartic acid | 1 g |
| HCA | 250 mg |
| ALC | 1 g |
| ALA | 150 mg |
| TMG | 750 mg |
| Choline | 250 mg |
| Myo-inositol | 600 mg |
| Coenzyme Q10 | 100 mg |
| Guggulipid | 750 mg |
| Tocotrienols | 50 mg |
| Biotin | 1 mg |
| Folate | 1 mg |
| Pantothenic acid | 50 mg |
| Pyridoxine | 50 mg |

A dose may also include conjugated linoleic acid (CLA):

| | |
|---|---|
| CLA | 1 g |

By its activation of peroxisome proliferator associated receptors (PPAR), CLA further enhances beneficial effects upon hepatic fat oxidation and VLDL secretion.

Agents chosen for this formulation were selected for their ability to effect a reduction in high-energy electron flux, as well as for concomitant secondary actions, which act to prevent the development of hyperlipidemia. Pyruvate and aspartic acid were both chosen to activate the generation of OAA, thereby facilitating the flux her high-energy electrons through thermogenic pathways. The resulting increased flux of high-energy electrons into thermogenic pathways enhances hepatic fat oxidation and is associated with diminished hepatic synthesis and secretion of very low-density lipoproteins (VLDL). Pyruvate further increases hepatic fat burning by independent activation of the dihydroxyacetonephosphate-alpha glycerolphosphate shuttle. This has synergistic beneficial actions upon hepatic VLDL secretion. Pyruvate and aspartic acid also contribute to weight loss. This weight loss acts independently to prevent hyperlipidemia, and also down-regulates hepatic lipoprotein synthesis and secretion. Choline increases endogenous carnitine levels and bioavailability, which further augments hepatic fat oxidation. This also improves the hyperlipidemic state. This activity is indirectly synergistic with the pyruvate action upon lipoprotein synthesis and secretion.

Example 5

An exemplary embodiment in accordance with the invention was formulated to inhibit the development of Type II diabetes using metabolic uncoupling therapy (MUT). Type II diabetes is a prototypical disorder manifesting increased electron pressure. MUT is, therefore, especially well-suited for its therapy. Two doses per day are recommended. Each dose includes:

| | |
|---|---|
| Coenzyme Q10 | 30 mg |
| R alpha lipoic acid | 300 mg |
| EPA | 200 mg |
| Chromium | 100 mcg |
| Selenium | 100 mcg |
| Aspartate | 2 g |
| Biotin | 1 mg |
| Creatine | 500 mg |
| L-Arginine | 1.5 g |
| Pyridoxine | 50 mg |
| Folic acid | 1 mg |
| Thiamine | 100 mg |
| Carnitine | 500 mg |
| TMG | 500 mg |
| Glycerylphosphorylcholine | 500 mg |
| Phosphatidyl Choline | 500 mg |

Several of the chosen agents have known properties that act to prevent the development of Type II diabetes by means unrelated to their metabolic uncoupling actions. Coenzyme Q10 is a mitochondrial anti-oxidant and membrane stabilizer. It also facilitates pancreatic insulin release. EPA and aspartate have potent weight loss effects. Obesity plays a key role in the development and progression of Type II diabetes and weight loss is a cornerstone of anti-diabetic therapy. Creatine lowers homocysteine levels. This reduces the inflammatory state that is a recognized risk factor for the development and progression of Type II diabetes. R-alpha lipoic acid improves insulin sensitivity and markedly diminishes the probability of developing Type II diabetes. Selenium is also a potent insulin sensitizing agent and acts synergistically with ALA. ALA also is therapeutic for diabetic neuropathy. Since redox stress is one of the early markers of the diabetic state, the utility of a program designed to modulate specifically and beneficially this pathophysiologic condition in numerous, complementary ways offers benefits not otherwise disclosed in the prior art.

Example 6

An exemplary embodiment in accordance with the invention was formulated for treating inflammatory gastro-intestinal disease using metabolic uncoupling therapy (MUT). Two doses per day are recommended. In addition to facilitating MUT, several agents from specific groups central to the invention were chosen because they possessed additional helpful, secondary properties of benefit in the therapy of inflammatory gastro-intestinal disease. These include EPA, which reduces the incidence of mucosal polyp formation. Phosphatidyl choline, in addition to its primary actions, reduces inflammation due to aspirin and NSAIDs (non-steroidal anti-inflammatory drugs). Stress frequently accompanies inflammatory intestinal disease. Pyridoxyl phosphate down-regulates stress-mediated pathways. Higher doses of choline and PC were utilized because of the large size of the lesions. Each dose includes:

| | |
|---|---|
| Phosphatidyl choline | 4 g |
| Choline | 2 g |
| Glycine | 500 mg |
| Glutamine | 2 g |
| R alpha lipoic acid | 100 mg |
| Niacin | 200 mg |
| Folate | 1 mg |
| Pyridoxal phosphate | 50 mg |
| SAMe | 100 mg |
| ALC | 150 mg |
| CLA | 2 g |
| EPA | 2 g |
| Green tea leaf extract | 50 mg |
| Vitamin B12 | 100 mcg |
| Vitamin A | 2500 IU |
| Vitamin D | 400 IU |
| Vitamin E | 200 IU |

The development of cognitive dysfunction is often associated with a fall in intra-neuronal NAD+ concentration. Oral provision of niacinamide as a single agent tends to improve NAD+ levels. There are, however, more effective mechanisms for maintenance of NAD+ levels in neurons than just isolated administration of niacinamide. The mechanisms are also associated with less toxicity. The related molecular mechanisms influence NAD+ levels as well as mechanistically related pathways. A synergistic combination of MUT agents maximizes therapeutic efficacy and minimizes toxicity. MUT compositions are based upon a detailed understanding of metabolic pathways involving the flux of high-energy electrons and their relationship with NAD+ metabolism. The choice of niacinamide as an NAD+ precursor is appropriate because of its enhanced uptake by the brain. However, the sole administration of niacinamide is inappropriate because even very high dosing lacks the therapeutic action of a directed multi-modal approach. Single drug therapy is also accompanied by toxicity in a large percentage of potential candidates for such treatment.

Example 7

An exemplary embodiment was formulated in accordance with the invention to enhance cognitive function. Four tablets per day are recommended. These may be administered in a divided fashion as two tablets twice per day. The inclusion in the formulation of relatively small doses of multiple, active agents, each of which beneficially modulates the involved pathways, obviates the usage of high doses of a single (potentially toxic) agent. A fall in NAD+ concentration results from a lack of adequate amounts of precursor, from deficient activation and transformation of the substrate into NAD+, from excessive destruction or consumption of any NAD+ present, and from improper metabolism in the involved pathways. Thus, there are a number of sites available for safe intervention to augment NAD+ levels. In addition to the multiple sites available for therapeutic intervention, there exist multiple ways to beneficially enhance NAD+ levels at each locale utilizing principles inherent in MUT. Four tablets include:

| | |
|---|---|
| Glycerylphosphorylcholine | 1,000 mg |
| Creatine | 1,000 mg |
| ALC | 500 mg |
| ALA | 100 mg |
| Folic acid | 800 mcg |
| B2 | 30 mg |
| Niacinamide | 200 mg |
| B6 | 100 mg |
| B12 | 5 mg |
| Thiamine | 25 mg |
| Coenzyme Q10 | 50 mg |
| Phosphatidyl choline | 50 mg |
| Choline | 500 mg |
| TMG | 100 mg |
| Pyruvate | 150 mg |

Group 1 agents oxidize the NADH/NAD+ couple, thus augmenting NAD+ levels. The specific agents chosen have a predilection for localization in the brain. This increases the local brain concentration at the active site. They also play additional key roles in brain metabolism in states characterized by falling NAD+ levels. These include metabolism of membranes, neurotransmitter production, and energy generation.

Additional beneficial, synergistic actions of the agents specifically chosen for this formulation are discussed below. Lipoic acid (ALA) and coenzyme Q10 were both included for their effects upon NAD+. Lipoic acid facilitates cerebral energy generation as a cofactor in enzymes involving these processes. It also acts as a detoxifying agent and facilitates the metabolism of glucose, the predominant fuel source in the brain. Creatine improves cerebral energy generation. ALC improves brain energy production and acts as a source of acetyl groups. It up-regulates CoA levels and activates the pyruvate dehydrogenase complex (PDH). This is the primary regulatory enzyme in the pathway of oxidative glucose metabolism. Coenzyme Q10 increases the number of mitochondria in neurons, is a mitochondrial electron chain constituent, and a mitochondrial anti-oxidant. Niacinamide is a direct precursor of NAD+, but was able to be used in smaller, safer amounts than typically used in the prior art. Other B vitamins, key players in cerebral energy generation as well as active MUT agents, were also included. Vitamin B6 helps protect the brain against the stress of falling NAD+ concentrations. The benefits of a MUT formulation over prior art include expanded safety profile, enhanced efficacy, utility of synergistic primary and secondary actions, and enhancements based upon specific tissue compartmentalization and augmented concentrations at the active sites.

Example 8

An exemplary embodiment in accordance with the invention was formulated as a brain performance-enhancing drink mix. This is preferably used during athletic competitions, such as golf matches, under stressful work conditions, around school exam times, or in other similar circumstances. One or two doses per day are recommended. An individual dose includes:

| | |
|---|---|
| NaCl | 225 mg |
| NaHCO₃ | 175 mg |
| K₂HPO₄ | 75 mg |
| KHCO₃ | 175 mg |
| MgSO₄ | 150 mg |
| Mg citrate-monohydrate | 100 mg |
| Glucose | 10 g |
| Lipoic Acid | 25 mg |
| Phosphatidyl choline | 100 mg |
| ALC | 40 mg |
| Mg-creatine chelate | 2 g |
| TMG | 100 mg |
| Choline | 100 mg |
| Glycine | 50 mg |
| Huperzine A | 50 mcg |
| Chromium | 50 mcg |
| Selenium | 50 mcg |
| Thiamin | 50 mg |
| Niacinamide | 150 mg |
| Pantothenic acid | 30 mg |
| Riboflavin | 20 mg |
| Pyridoxal phosphate | 20 mg |
| Vitamin B12 | 5 mg |
| Folic acid | 1 mg |
| Natural cherry flavor | |

As stated above, this product is primarily, although not exclusively, designed for use to enhance brain function during stressful periods. At these times, cortisol levels are frequently elevated. Under these conditions, the ability of the brain to use glucose, its main fuel source, is impaired. This exacerbates situations of inadequate fuel supply, deficiencies in energy production, neurotransmission, excessive free radical production and membrane repair. In a comprehensive approach in accordance with the invention, each of these abnormalities is addressed. This leads to stacking the formulation with MUT agents that address the primary problem. Since there are simultaneously quite broad requirements in many other areas of brain metabolism, the agents chosen have multiple beneficial functions that address these needs cogently. In addition, the selected agents preferably cross the blood-brain barrier easily.

Because glucose availability and metabolism are important in this situation, glucose was included as an ingredient in the formulation. Pyridoxal phosphate was included for its beneficial modulation of the stress state and elevated cortisol concentrations. Since energy generation was impaired, all the B vitamins were included for their secondary roles in energy generation, as well as for their primary roles in modulation of high-energy electron flux. Chelated magnesium creatine was included not only for its ability to augment methyl group availability, but also to improve cerebral energy generation directly. Magnesium is important for many steps in energy production. ALA is multifunctional in these circumstances. It helps with energy generation, redox status, inflammation, transition metal handling, and in a role as an anti-oxidant that easily crosses into the brain and has activity in the cytosol as well as in lipid domains. Huperzine A crosses easily into the brain and improves cholinergic neurotransmission. ALC provides acetyl groups, up-regulates CoA levels, and improves cerebral energy generation. Choline acts as a precursor for the neurotransmitter acetylcholine and membrane phospholipids. Lipoic acid increases intracellular glutathione levels. This facilitates cellular anti-oxidant function. As may be seen in this example, the complexity of the problem was evaluated and the composition of the formulation was developed in accordance with the invention to address the complex problem.

Various neurodegenerative disorders are amenable to combinations of MUT agents. Such disorders include multiple sclerosis and Alzheimer's disease, but MUT formulations are applicable generally to a broad range of similar disorders. Many neurodegenerative disorders are characterized by the accumulation of non-digestible cellular remnants. These may form as the result of non-enzymatic oxidative cross-linking reactions that metabolically transform proteinaceous or other compounds into waste products that build up over time. These disorders are called proteopathies.

Multiple sclerosis is generally believed to be an inflammatory disorder of unknown etiology affecting the myelin sheath of nerves. Sphingomyelin is one of the major lipids in the myelin sheath. It is also an endogenous electron-accepting compound (analogous to the Group 1 MUT compounds described in the specification) and acts as a sink for high-energy electrons. Sphingomyelin's principal biological function is to enable nerve cell transmission by its action in the myelin sheath. If it is consumed while acting as a protective high-energy electron-accepting compound, it is no longer available to perform its main function, and nerve damage occurs.

Hydroxyl ions have significant reducing potential, as shown by their detoxification via reaction with the oxidized disulfide groups in albumin. Hydroxyl ions are present in the inflammatory reaction seen in multiple sclerosis. They play a key role in myelin breakdown. When present in sufficient quantity, sphingomyelin binds the high-energy electrons supplied by the hydroxyl ions in a sacrificial act that neutralizes the hydroxyl radical. The sphingomyelin is consumed in the process, thereby degrading the structure and function of the myelin sheath.

Selected MUT agents also quench hydroxyl ions (e.g., through the tendency of hydroxyl ions to react with the positive nitrogen atom in the trimethylnitrogen moieties in the structures of the Group 1 agents). As this happens, methane is released. The anti-reductant agents thereby serve as sacrificial neutralizers of the hydroxyl ions (or other ROS). This inhibits or prevents the loss of sphingomyelin and preserves the integrity of the myelin sheath.

In Alzheimer's disease, decreases in the acetylcholine content of the brain are an early, and consistent, finding associated with disastrous functional consequences. Oxidative stress has been implicated early in the course of Alzheimer's disease, and hydroxyl ion activity has also been documented. Acetylcholine, like sphingomyelin, has a positively charged trimethylnitrogen group and in all likelihood sacrifices itself as a partial defense against deleterious compounds possessing unpaired electrons. This adversely affects the function of cholinergic (acetylcholine mediated) neurotransmission. This neurological system helps mediate memory function and cognitive processing. Therapy for Alzheimer's disease, in accordance with the invention, utilizes combinations of electron-accepting compounds. They function as substitute electron acceptors for the acetylcholine molecules. In so doing, the acetylcholine molecules are preserved for their primary functions in the brain.

Apoptosis is another common feature of neurodegenerative processes. It is a delayed form of cell death brought about by activation of an energy-requiring suicide program inherent in multicellular organisms. Various mechanistic explanations for this exist, but the exact pathways involved are not fully understood. Elevated NAD+ levels are involved in DNA repair. DNA damage (as seen in states of oxidative stress) is known to activate poly (ADP-ribose) polymerase (PARP), which utilizes NAD+ as a substrate. This results in NAD+ depletion, and subsequently ATP depletion, due to futile activation of energy-consuming NAD+ re-synthetic pathways. ATP depletion is known to be one of the central factors leading to the induction of apoptosis. Reductive stress, in the presence of oxygen, typically generates ROS, including hydroxyl radicals. This may activate apoptotic pathways.

Nerve growth factor (NGF) is one of the only known agents that prevents apoptosis of cells in culture. Currently, NGF must be administered by intracranial injection. This provides a significant impediment for broad clinical utility. In contrast, MUT agents which increase NAD+ (and thus decrease the NADH/NAD+ ratio), may be taken orally and have easy access to the central nervous system. Augmentation of NAD+ levels prevents DNA damage. In addition, NAD+ has been reported to inhibit calcium-magnesium endonuclease, which fragments DNA when it is activated during the apoptotic process. High NAD+ levels also facilitate DNA repair. The anti-reductant activity of individual agents in Groups 1 to 6 increases NAD+ levels.

Example 9

A multifunctional combination for augmenting NAD+ levels was formulated. Typically it is administered two to three times per day for an effective period of time. One dose includes:

| Niacinamide | 500 mg |
| ALC | 500 mg |
| Myo-inositol | 250 mg |
| Choline | 250 mg |
| Phosphatidyl choline | 500 mg |
| Glycine | 50 mg |
| Lipoic acid | 100 mg |
| Coenzyme Q10 | 30 mg |
| Vitamin B1 | 10 mg |
| Pyridoxine | 10 mg |
| Pantothenic acid | 10 mg |
| Glycerylphosphorylcholine | 150 mg |
| EPA may also be included | 100 mg |

This formulation is heavily stacked with sacrificial electron-accepting agents, each of which are able to recycle NADH to NAD+. Their similar biochemical functions act synergistically in this regard. This fact, coupled with their quite different chemical structures, enables this composition to function effectively in the various intra-cellular compartments occupied by the various agents.

High levels of NAD+ also stimulate other important pathways such as glycolysis. Up-regulation of glycolysis increases the production of ATP. In addition, NAD+ is a feedback inhibitor of phosphoribosyl transferase, the rate-limiting enzyme in the synthesis of NAD+, a process that consumes ATP. Therefore, increasing the level of NAD+ results in sparing of ATP and enables cells to better combat an oxidative insult while maintaining redox homeostasis.

Administration of nicotinamide, an MUT agent, is effective for maintaining appropriate neuronal NAD+ levels. In addition, supplementation with nicotinamide augments NADPH, which is associated with maintenance of intracellular glutathione levels, decreased DNA fragmentation, and preservation of ATP, as well as preservation of nerve cell structure and function.

Metabolic uncoupling therapy provides useful therapeutic strategies for treatment of other diseases involving neurodegeneration, such as Huntington's disease and mitochondrial encephalopathy with stroke-like symptoms. MUT is useful for treating neurological disorders including various types of traumatic conditions, stroke, hemorrhage, neoplasia, generalized cerebral edema, and iatrogenic damage from neurosurgical procedures.

Example 10

A specific formulation designed to protect the brain during a neurosurgical procedure was prepared. Typically, a single dose is given before surgery and then repeated every six hours for 72 hours or longer after the conclusion of the operation. One dose contains:

| Mannitol | 30 g |
| Mg-Creatine | 5 g |
| ALC | 1 g |
| Phosphatidyl choline | 2 g |
| Glycerylphosphorylcholine | 1 g |
| Choline | 250 mg |
| Lipoic acid | 1 g |
| Niacinamide | 1 g |
| Pyridoxine | 50 mg |
| Thiamin | 100 mg |
| Pantothenic acid | 50 mg |
| Pyruvate | 5 g |
| Green Tea Leaf extract | 100 mg |
| Vitamin C | 500 mg |
| Vitamin E | 100 IU |
| Coenzyme Q10 | 300 mg |

In addition to facilitating the handling of high-energy electron flux via MUT, this formulation addresses other issues, including control of brain edema, exhaustion of NAD+, oxidative stress, hydrogen ion handling, cerebral energy generation and glucose metabolism. As a result, the outcome from neurosurgery improves.

According to the free radical theory of aging, oxidative metabolism in aerobic cells is accompanied by the reduction of oxygen to superoxide radical, hydrogen peroxide and hydroxyl radical. These ROS cause damage to cellular components, particularly nuclear and mitochondrial DNA. This leads to impaired function, increased somatic mutations and hence to degeneration and aging. Mitochondria are the main source of cellular ROS generation due to an electron leak from ubisemiquinone or other semiquinone moieties in the electron transport chain. Evidence that this ROS production is related to aging includes the observation that production of ROS is higher in animals with shorter maximal lifespan.

Cells have powerful anti-oxidant defenses to protect themselves against damage from ROS. The attention in the field has been focused on these anti-oxidants. On the other hand, regulation of the generation of ROS has been neglected despite the fact that prevention, rather than cure, is a more logical way to ameliorate oxidative damage. Uncoupling agents or increases in ADP reduce ROS production in isolated mitochondria. ROS production is strongly dependent upon the mitochondrial proton motive force (PMF). PMF affects ROS production by altering the redox state of coenzyme Q. At high PMF, respiration slows. As a result, electrons accumulate on coenzyme Q10, thereby increasing the concentration of ubisemiquinone, instead of passing down the electron transport chain to the terminal electron acceptor, oxygen. This increases the instantaneous concentration and half-life of ubisemiquinone, thereby increasing mitochondrial ROS generation.

Metabolic uncoupling agents in accordance with the invention lower PMF by limiting the flux of high-energy electrons down the ETC. Various mechanisms accomplish this. This may be achieved in accordance with the invention by substrate-mediated electron transport between mitochondria and cytosol. Substrate-mediated electron transport between mitochondria and cytosol is associated with processes that: 1) "discount" the energetic status of these electrons (i.e., NADH is metabolized to $FADH_2$ via the alphaglycerophosphate-dihydroxyacetonephosphate shuttle), or 2) engage in futile metabolic pathways that consume ATP, increase ADP and thereby collapse the PMF.

Without being bound to any particular theory, metabolic uncoupling includes an alternative electron-acceptor substrate that binds and neutralizes, or alternatively, transports high-energy electrons out of the mitochondria. As part of the malate/aspartate shuttle, malate is transported across the mitochondrial membrane in exchange for aspartate. Oxaloacetate (OAA) is generated in mitochondria via the carboxylation of pyruvate by the enzyme pyruvate carboxylase (PC), or the transamination of aspartate. OAA then acts as the alternate electron acceptor in a reaction that generates malate. Malate then transports the electrons into the cytosol across the mitochondrial membrane (that is otherwise impermeable to electrons). Hence, pyruvate and aspartate, as well as serine or glycine, facilitate the "diversion" of high-energy electrons into the cytosol. In the cytosol, the electrons enter futile ATP-consuming metabolic cycles, or alternatively, the electrons are transported back into mitochondria in a "discounted", or lower energy, form as FADH2, as described above. These processes serve to collapse the PMF, with subsequent beneficial effects of decreasing the generation of ROS.

Another mechanism in accordance with the invention tending to decrease PMF levels and produce a relative oxidation of coenzyme Q is the transfer of high-energy electrons to electron acceptors (designated here by the letter R) that act as sacrificial molecules, thus generating an electron sink.

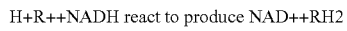

H+R++NADH react to produce NAD++RH2

This mechanism is activated by the use of sacrificial anhydride acceptors (depicted by the letter R above), rather than oxygen, as the terminal electron acceptors. Examples of such compounds are the redox-active MUT agents included in Groups 1, 3, 5 and 6, as described in this specification. High doses of single agents pose the risk of undesirable side-affects. Therefore, in MUT as practiced in accordance with the invention, combinations of agents comprising specific ratios and precise amounts, depending on the particular selected mechanistic approach and on the desired result, are recommended to maximize efficacy and minimize undesirable side effects. Use of a synergistic combination of multiple agents in relatively small, safe doses formulated in accordance with the invention circumvents the problem of toxic side effects.

Thus, at least two mechanisms for decreasing ROS levels are provided by metabolic uncoupling therapy in accordance with the invention. These mechanisms, either alone or in combination, act "upstream" in the oxidative stress-generating pathway. Prior art suggests the use of anti-oxidants to quench the damaging ROS present within cells, but it does not address the processes controlling the generation of these same ROS. Metabolic uncoupling therapy, as utilized in accordance with the invention, utilizes a methodology that acts upstream from, and precedes, the generation of these ROS. Thus, similar to other approaches of preventative medicine, MUT safely and effectively down-regulates the production of ROS and thereby the aging process itself.

There are additional synergisms, for example, involving the use of specific agents, such as acetyl L-carnitine ("ALC"), in this holistic approach. ALC is easily transported into the central nervous system and acts not only as a potent source of anhydride acceptors (carnitine), but also provides acetyl groups for energy generation and acetylcholine synthesis. The selection of a MUT agent that achieves a plurality of desirable effects (both regarding metabolic uncoupling as well as separate synergistic effects) is an important feature of embodiments in accordance with the invention.

The efficacy of interventions using MUT, which tend to keep ETC semiquinones in a relatively more oxidized state, parallel results achieved from one of the most successful anti-aging interventions known—that of caloric restriction. Both caloric restriction and MUT restrict the supply of high-energy electrons to the oxidized ubiquinone pool. Hence, MUT achieves anti-aging effects via mechanisms similar to those produced by caloric restriction, but without the necessity of imposing hunger.

Inflammation, oxidative stress and nitrogenous stress are key processes in both the intrinsic aging of skin, as well as photo-aging due primarily to sun exposure. Both intrinsic aging and photo-aging involve activation of panels of pro-inflammatory genes by oxidant-sensitive transcription factors, such as AP-1 and nuclear factor kappa B (NFKB). Hydroxyl groups are extremely active, short-lived ROS known to be generated by ultraviolet radiation (UV). They are important modulators of AP-1 and NFKB. As mentioned above, they have a significant reducing potential. Many substances containing reducible groups act as anti-reductants (agents that act to decrease, or diminish, reductive stress). For example, reductive addition of hydroxyl groups to double bonds of pyrimidines, pyrazines and other aromatic rings may be related to the beneficial action of water-soluble vitamins in free radical-induced stress. Similar reductive reactions are involved in the formation of hydroxy derivatives of nucleic acids, for example, of 8-hydroxy-2'-deoxyguanosine, which are incorrectly viewed in the prior art to be principally a result of oxidative stress. An important feature of embodiments in accordance with the invention is application of the concept that reductive stress, or reductive stress plus the addition of oxygen, rather than oxidative stress is the driving mechanism behind this tissue damage.

In embodiments in accordance with the invention for treating intrinsic aging and photo-aging, specific combinations, ratios and amounts of MUT agents intervene to protect the vital nucleic acids, proteins and lipids that would otherwise be damaged. Skin-care and anti-aging embodiments in accordance with the invention include topical application of MUT agents. Additionally, certain embodiments utilize liposomal delivery systems and other absorption enhancers.

Example 11

An exemplary embodiment in accordance with the invention was formulated for skin care and anti-aging effects using metabolic uncoupling therapy. A liposomal delivery system was optional. In addition to the specific metabolic uncoupling properties, additional properties of the MUT agents that are functionally synergistic with the metabolic uncoupling functions were reasons for their selection. These include the fact that lipoic acid is both fat and water-soluble and is therefore readily absorbed transcutaneously. It also has many anti-inflammatory activities. TMG helps preserve skin barrier function. Phosphatidyl choline facilitates the transport and absorption of many of the other ingredients. Coenzyme Q10 is a membrane-active agent. The exemplary formulation is utilized locally on the appropriate skin areas several times per day for an appropriate period of time.

One 2 oz. Jar contains:

| | |
|---|---|
| R alpha lipoic acid | 2 g |
| Coenzyme Q10 | 1 g |
| TMG | 1 g |
| Carnitine | 1 g |
| Phosphatidyl choline | 3 g |
| Nicotinamide | 1 g |
| Glycerylphosphorylcholine | 1 g |
| Etidronic acid | 600 mg |
| Green tea leaf extract | 500 mg |
| Vitamin E oil | 4 g |
| CLA | 4 g |
| Medium chain triglycerides | 4 g |
| Kojic acid | 500 mg |
| Retinyl palmitate | 1 g |
| Niacin | 500 mg |
| Folate | 5 mg |
| Pyridoxine | 100 mg |
| Glycine | 100 mg |
| Arginine | 200 mg |
| Aloe vera gel | 20 g |
| Jojoba oil | 24 g |

A formulation also contains de-ionized water, glycerine, glyceryl stearate, PEG-100, stearic acid, dimethicone, and methyl paraben.

Metabolic uncoupling therapy in accordance with the invention is also useful for avoiding iatrogenic toxicity. Conditions exist in the prior art where proper medical interventions are associated with unavoidable toxicity. Cancer chemotherapy is one such situation. For example, Doxorubicin is an anti-proliferative agent that often causes cardiomyopathy and nephropathy. This is most likely due to reductive stress related to the dislocation of electrons by the induction of redox cycling. Anti-reductive MUT diminishes acute toxicity and aids in prolonged survival.

Example 12

A formulation was developed for protecting against toxicity secondary to redox cycling from agents like Doxorubicin. Suggested use is for at least 5 days following administration of the toxic agent, preferably two times to three times a day. Preferably, it is administered for 24 hours prior to administration of the redox-cycling agent.

| | |
|---|---|
| Phosphatidyl choline | 5 g |
| SAMe | 200 mg |
| Myo-inositol | 500 mg |
| Glycerylphosphorylcholine | 2 g |
| Niacinamide | 500 mg |
| Pyruvate | 2 g |
| Serine | 2 g |
| Albumin | 5 g |
| EPA | 2 g |
| GLA (gamma linolenic acid) | 600 mg |
| CLA (conjugated linoleic acid) | 1 g |
| Lipoic acid | 300 mg |
| Thiamin | 100 mg |
| Folk acid | 1 mg |
| L-carnitine | 2 g |

Other substances used in medical interventions in the prior art interrupt the flow of electrons along the electron transport chain. Included in this group are non-steroidal anti-inflammatory drugs (NSAIDs) and cyclosporine. Certain pro-inflammatory cytokines, such as TNFalpha, IL1 and IL6, have similar detrimental effects. These cytokines are present in infectious, neoplastic or inflammatory conditions, and are also seen status post organ-transplantation. In contrast, embodiments of MUT in accordance with the invention utilize potent anti-reductive capacities of numerous MUT agents combined in specific ways in association with their concomitant secondary beneficial actions. These formulations maximize efficacy while minimizing adverse side effects.

Metabolic uncoupling therapy is also useful for enhancing athletic performance and facilitating repair of exercise-related dysfunction and injury. Various combinations, amounts and ratios of the agents described herein have applicability in numerous pathways related to exercise and athletic performance. These may be subdivided generally into chronic effects and more acute effects. The former tend to be mediated by chronic modulation of enzyme levels, enzyme activities and gene transcription. The latter involve acute, real time modulation of various metabolic pathways. The artificial acute/chronic division merely facilitates descriptive mechanisms, and it is to be noted that there is significant overlap between the two. Discussion of chronic effects and acute effects serves to enhance understanding of the metabolic pathways involved and how they are influenced by MUT.

Modulation of high-energy electron metabolism and pathways impacts numerous mechanisms that influence athletic performance and function. Among other benefits and effects, these pathways involve beneficial modulation of energy generation, expansion of fuel stores, facilitated muscle recovery after exercise, enhanced coupling of cytosolic and mitochondrial energy-generating pathways, down-regulation of acidosis, improved myoskeletal efficiency, decreased formation of reactive oxygen species (ROS), down-regulation of inflammatory mediators and production of less tissue damage and soreness.

Ongoing ATP generation is up-regulated by keeping the NADH/NAD+ ratio in a more oxidized state. This enhances glycolytic as well as tricarboxylic acid cycle activity. Enhanced glycolysis occurs simultaneously with a fall in lactate generation and enhanced endogenous generation of pyruvate. Acetyl L-carnitine (ALC), carnitine or pantothenic acid augment free CoA levels. Exogenous administration of pyruvate directly enhances pyruvate levels. These three effects (increased NAD+/NADH, increased CoA, increased pyruvate) stimulate the mitochondrial enzyme, pyruvate dehydrogenase (PDH), which facilitates coupling of glycolysis with tricarboxylic acid cycle activity. As a result, hydrogen ion concentration falls and pH is normalized. Since cellular handling of hydrogen ions is costly from an energetic perspective, the enhanced coupling of these two metabolic pathways markedly improves metabolic efficiency and hence muscular functional output.

The more-oxidized NADH/NAD+ redox couple also down-regulates NADH-dependant oxidase activity, which markedly decreases production of toxic ROS. This decreases vital tissue injury, enhances function, and acts to diminish one of the primary causes of delayed-onset muscle soreness (DOMS).

When utilized after exercise, combinations of MUT agents in accordance with the invention facilitate muscle recovery. This occurs by several processes: decreased ROS production diminishes DOMS; improved redox profile facilitates replenishment of energy supply; improved insulin sensitivity speeds up glycogen repletion and has both anabolic and anti-catabolic effects upon protein synthesis; and resolution of lactate build-up and acidosis is accelerated.

Example 13

An exemplary embodiment emulation in accordance with the invention facilitates post-workout muscle recovery. During high-intensity muscular workouts, many events occur that stress the functional and anatomic properties of the musculo-skeletal system. Large volumes of muscular work being performed require the generation of large numbers of high-energy electrons to fuel the process. In addition, during high-intensity exercise, the rate of muscular work being performed frequently exceeds the ability of the blood supply to deliver oxygen. This creates a situation where high-energy electrons are being rapidly generated at a time when there is insufficient oxygen present to act as the terminal electron acceptor for the high flux of electrons passing down the electron transport chain. This creates a condition which induces reductive stress in the muscle cell. As oxygen again becomes available, the glut of high-energy electrons is transferred non-enzymatically to oxygen. This results in the creation of superoxide radicals and many other ROS.

The deleterious effects of this process are greatly magnified in the presence of free iron. Under these circumstances of (relative) ischemia/reperfusion, free iron is generated upon the reduction of ferric to ferrous iron. When this happens, the ferrous iron is released from its binding protein and free iron is generated. Free iron then catalyzes the formation of many more ROS. The end result of these processes is the development of a destructive pro-inflammatory state in the muscle. This produces muscle damage, impaired performance, muscle soreness, predisposition to injury and a prolonged recovery period. To treat the development of these numerous conditions effectively, it is important to understand the mechanisms responsible for their development. These mechanisms cause a mismatch between the generation and the safe metabolism of large numbers of high-energy electrons in the affected muscles. This results in the formation of a large pool of high-energy electrons that initiates multiple damaging pathways. MUT ameliorates the excessive flux of electrons and the damage it produces. Since the forces which generate the reductive stress are of large magnitude, the exemplary MUT formulation includes relatively high doses and large numbers of active agents in the composition. Multiple high doses of most of the Group 1 agents were chosen. The main reasons for not choosing the other Group 1 agents relate to absorption and ease of use. Green tea leaf extract was chosen to bind free iron, as well as for potent anti-oxidant activity. Choline and carnitine were chosen together because of the beneficial effect of choline upon carnitine levels. Choline also acts as a precursor for acetylcholine, the neurotransmitter at the musculo-skeletal junction. Phosphatidyl choline augments these same processes and in addition facilitates membrane function and repair mechanisms. ALA has additional benefits regarding energy generation, iron metabolism, and glucose metabolism. The B vitamins chosen are used in high doses. In addition to their metabolic-uncoupling activities, they play important secondary roles in energy generation, stress modulation, glucose metabolism, and in the many avenues of cross-talk necessary for synergistic interaction. Pyruvate also enhances the activity of the enzyme PDH, as does carnitine (indirectly via elevation of CoA levels), thus better coupling the production and consumption of hydrogen ions. This beneficially modulates adverse pH effects. Creatine was included because of its beneficial modulation of energy state and the enzyme AMPK.

An individual post-exercise dose contains:

| | |
|---|---|
| NaCl | 331 mg |
| NaHCO$_3$ | 252 mg |
| K2HPO$_4$ | 100 mg |
| KHCO$_3$ | 100 mg |
| MgSO$_4$ | 180 mg |
| Mg citrate | 1400 mg |
| R alpha lipoic acid | 25 mg |
| Chromium | 100 mcg |
| Green tea leaf extract | 50 mg |
| ALC | 100 mg |
| Phosphatidyl choline | 250 mg |
| L-carnitine | 25 mg |
| Selenium | 100 mcg |
| Choline | 100 mg |
| Myo-inositol | 500 mg |
| TMG | 250 mg |
| Pyruvate | 250 mg |
| Creatine | 1 g |
| B1 | 50 mg |
| B2 | 50 mg |
| B3 | 100 mg |
| B6 | 50 mg |
| B12 | 5 mg |
| Vanadyl sulfate | 100 mcg |
| Glucose | 30 g |
| Whey protein | 1 g |
| BCAA | 500 mg (BCAA = branched chain amino acids) |
| Glutamine | 375 mg |
| L-arginine | 250 mg |
| Natural orange flavor | |

Example 14

An exemplary embodiment in accordance with the invention was formulated as a sports performance drink mix. Similar considerations apply here as were involved in Example 13 above. Special considerations for a drink mix that is to be consumed shortly before, or during, a sporting event address issues including rapidity of absorption, gastric emptying, and stomach fullness, and are heavily influenced by energy generation and transduction concerns, and electrolyte shifts. These considerations explain some of the differences between the two formulations. An individual dose contains:

| | |
|---|---|
| NaCl | 331 mg |
| NaHCO$_3$ | 300 mg |
| K2HPO$_4$ | 150 mg |
| KHCO$_3$ | 150 mg |
| MgSO$_4$ | 260 mg |
| Mg citrate | 300 mg |
| Vitamin C | 50 mg |
| Chromium | 50 mcg |
| Selenium | 50 mcg |
| Vanadyl sulfate | 60 mcg |
| Pyruvate | 150 mg |
| Carnitine | 25 mg |
| Choline | 75 mg |
| Myo-inositol | 300 mg |
| TMG | 150 mg |
| Alpha lipoic acid | 20 mg |
| Glucose | 30 g |
| Phosphatidyl choline | 200 mg |
| BCAA | 150 mg |
| Glutamine | 125 mg |
| L-arginine | 100 mg |
| Thiamin | 10 mg |
| Ribose | 25 mg |
| Niacin | 25 mg |
| Vitamin B6 | 10 mg |
| Natural cranberry flavor | |

Example 15

An exemplary embodiment in accordance with the invention was formulated as a muscle-building powder drink mix. There are overlapping considerations involving this example and Examples 13 and 14 above. Here the focus is upon the building of muscle, not sports performance or muscle recovery after an exhaustive workout. While similar considerations regarding high intensity muscle work as were outlined in Example 13 are relevant, the additional emphasis is upon the building of muscle, rather than the inhibition of its breakdown and recovery as were discussed above.

Muscle building relates to anabolic and vascular considerations and related issues. These considerations explain the changes in the Group 1 agents, amounts and ratios. Anabolic effects suggested the increase in the amount of creatine, the addition of taurine, the increase in BCAA, and the larger amount of the anti-catabolic agent glutamine. The inclusion of higher amounts of selenium, chromium, ALA and vanadyl sulfate were included to bolster the anabolic effects of the formulation by the insulin sensitizing action of these agents. The larger arginine dose, in conjunction with the actions of the insulin sensitizers, maximizes the blood flow to the involved muscles. This acts as a vascular traffic director by preferentially directing the remainder of the ingredients to the desired muscles. The result of these changes maximizes the local tissue concentrations of the active agents. This serves to magnify the end result while minimizing systemic toxicity. Prior art does not teach the use of this combinatorial approach for development of maximum synergy. One dose per day is recommended. A single dose includes:

| Ingredient | Amount |
| --- | --- |
| Creatine | 10 g |
| Mg citrate | 750 mg |
| ALC | 300 mg |
| Carnitine | 300 mg |
| Choline | 300 mg |
| Sphingomyelin | 400 mg |
| Chromium | 150 mcg |
| Selenium | 150 mcg |
| R alpha lipoic acid | 100 mg |
| Vanadyl sulfate | 150 mcg |
| Pyruvate | 500 mg |
| Vitamin B1 | 50 mg |
| Vitamin B2 | 50 mg |
| Niacinamide | 100 mg |
| Pyridoxine | 20 mg |
| Folk acid | 400 mcg |
| Glutamine | 2 g |
| L-arginine | 400 mg |
| Taurine | 250 mg |
| Pyruvate | 500 mg |
| BCAA | 500 mg |
| Strawberry flavor | |

Metabolic uncoupling therapy in accordance with the invention is useful for ischemia, ischemia/reperfusion injury and for preserving biological materials. Conditions of ischemia, hypoxia and/or anoxia are associated with reductive stress as the prime functional insult. The prior art taught that depletion of ATP was the primary functional insult. ATP depletion occurs because as adequate tissue oxygen tension is compromised, mitochondrial oxygen levels fall. Oxygen is the terminal electron acceptor in the respiratory process. In its absence, high-energy electrons (i.e., mitochondrial NADH) build up. This subsequently inhibits further generation of ATP and produces a host of damaging effects in the cell.

Upon reperfusion (i.e., after resolution of the occlusive or low-flow vascular state during which oxygen deprivation occurs, or when a preserved organ is transplanted from a donor to a recipient), the supply of oxygen is returned to the tissues. The combination of a high NADH/NAD+ ratio with high tissue-oxygen levels (associated with reperfusion) generates a proliferation of ROS that play a central role in causing I/R injury and acute transplantation-associated organ insult. Analysis of the relevant metabolic pathways shows the benefits of modulating the NADH/NAD+ ratio with specific agents in precise amounts and ratios in accordance with the invention.

Beneficial actions of these formulations modify effects that occur acutely and also modulate more sub acute or chronic processes. Acute effects include, among other things, handling of hydrogen ions, prevention of disconjugation of anaerobic glycolysis and glucose oxidation, regulation of the nucleotide transporter, calcium metabolic aberrations, mechanisms of Na-Ca exchange and other related metabolic pathways. More chronic processes include production of free radicals, subsequent oxidation of membrane lipids, DNA, RNA, and protein moieties, activation of pro-inflammatory transcription factors and production of clinical symptoms.

Example 16

An exemplary embodiment in accordance with the invention was formulated as a biological preservation solution. The basic issue here involves the removal of biologic materials from a donor and subsequent re-implantation into a recipient. During the intervening time, the tissue is without blood supply and is un-oxygenated. This defines a situation of ischemia/reperfusion and, as such, the physiologic arguments outlined above apply. The additional constraints involving agent choices pertain to safety considerations pertinent at the time the biologic material is re-implanted.

Ingredients per liter of solution:

| Ingredient | Amount |
| --- | --- |
| Pyruvate | 5 g |
| Choline | 1 g |
| TMG | 750 mg |
| Vitamin B1 | 200 mg |
| ALC | 1000 mg |
| Lipoic acid | 5 g |
| Carnitine | 1,000 mg |
| Vitamin B3 | 1,000 mg |
| Vitamin B5 | 100 mg |
| NACL | 75 mg |
| $K_2HPO_4$ | 300 mg |
| Mg citrate | 1,000 mg |
| $NaHCO_3$ | 150 mg |
| Glucose | 20 g |
| Penicillin | 500 mg |
| Insulin | 20 units |

A preferred embodiment may include amiloride or calcium channel blockers in clinically recommended dosages.

Functional foods in accordance with the invention are formulated by incorporating MUT agents into food and nutritional products. For precise metabolic control of high-energy electron metabolism and handling, specific combinations of MUT active agents are included in bars, drinks, shakes, cookies, salad dressings and the like and thereby constitute a new category of functional foods.

For example, low-fat salad dressings generally include high amounts of refined carbohydrates, which are associated with the development of insulin resistance, elevation of serum triglyceride (TG) levels, lowered HDL (high density lipoprotein), and the development of an atherogenic, small, dense LDL (low density lipoprotein) profile. Monounsaturated fat, such as is found in olive oil, has beneficial effects upon metabolic health in these circumstances and also facilitates the absorption of the phytonutrients in the salad. However, it is higher in calories since fat contains 9 calories per gram, whereas carbohydrates contain only 4 calories per gram. The inclusion of specific amounts, ratios and types of metabolic uncoupling agents as described herein acts to diminish possible weight gain associated with these otherwise nutritional products, especially if they are used liberally.

Without reference to specific mechanisms, fatty acids are metabolized to carbon dioxide and water in association with the generation of high-energy electrons derived from beta-oxidation and the tricarboxylic acid cycle. For the most part, they exist in the form NADH. As these electrons are passed on to oxygen via the electron transport chain, ATP is generated. Precursors of OAA (such as the agents of Group 4) act as electron acceptors. When used as supplements in accordance with the invention, they facilitate the transfer of electrons from NADH to OAA (which is generated, for example, by the provision of pyruvate or aspartate) with subsequent generation of malate. Malate is subsequently transported to the cytosol. This comprises a substrate-driven electron shuttle from the mitochondria to the cytosol, bypassing electron transfer to oxygen. Once in the cytosol of the hepatocyte, these reducing equivalents may participate in energy-consuming thermogenic futile cycles, which allow the oxidation of fat and the release of energy as heat. These processes are enhanced by specific combinations of carnitine, Group 4 agents, biotin, hydroxycitrate and other anti-reductive agents, which function as electron sinks, facilitating futile metabolic cycles, increasing CoA levels and inducing elevation of ADP. These combinations, in accordance with the invention, are designed to augment thermogenic (energy-wasting) activity and caloric expenditure, which burn excess calories and contribute to weight loss.

Example 17

An exemplary embodiment, in accordance with the invention, was formulated as a salad dressing mixture. Agent choices were made using a methodology as described above in previous examples. In addition, phosphatidyl choline was included because of its ability to function as an emulsifier. ALC additionally raises CoA levels. L-carnitine facilitates transport of fat into the cellular furnaces for combustion. The following mixture of ingredients is added to 2 oz. of vinegar and olive oil salad dressing:

| | |
|---|---|
| Phosphatidyl choline | 50 mg |
| R alpha lipoic acid | 3 mg |
| TMG | 5 mg |
| Myo-Inositol | 10 mg |
| ALC | 1 mg |
| CLA | 10 mg |
| Pyruvate | 50 mg |
| Biotin | 600 mcg |
| L-carnitine | 10 mg |
| *Garcinia cambogia* extract | 20 mg |
| Chromium polynicotinate | 10 mcg |
| Niacin | 10 mg |
| Pantothenic acid | 20 mg |
| Riboflavin | 20 mg |

A formulation optionally contains Mag-creatine.

| | |
|---|---|
| Mg-creatine | 1 g |

The inclusion of the creatine, in association with the acetic acid in the vinegar, activates the fat burning enzyme AMPK. This provides additional beneficial synergies that promote further fat burning.

Example 18

An exemplary embodiment in accordance with the invention was formulated as a supplementary additive to a protein bar. The composition is based upon factors similar to those in Example 17, but also includes the potential for additional healthy metabolic modulation. This specifically relates to improvements in insulin sensitivity with subsequent benefits in the constellation of symptoms known as the insulin resistance syndrome (IRS).

In addition to the beneficial modulation of fat burning pathways, as seen in prior examples, the protein bar additives were chosen also to improve IRS symptomatology. This involves up-regulation of the electron-sink pathways, improvement in insulin sensitivity, and beneficial vascular effects.

Creatine was chosen because, in addition to its ability to facilitate MUT, it lowers homocysteine levels. This is beneficial for the heart. Biotin lowers hepatic glucose output, which stabilizes glucose levels. This improves carbohydrate metabolism in general. Higher levels of each Group 1 agent were utilized. Higher ALA doses were used because ALA is a potent insulin sensitizer. The spice cinnamon was added because in addition to being a flavoring agent, it also augments insulin sensitivity. The following ingredients are included in one low carbohydrate/high protein bar:

| | |
|---|---|
| Creatine | 250 mg |
| Carnitine | 20 mg |
| Acetoacetate | 100 mg |
| R alpha lipoic acid | 10 mg |
| Phosphatidyl choline | 200 mg |
| ALC | 25 mg |
| Myo-inositol | 50 mg |
| TMG | 50 mg |
| Vitamin B2 | 5 mg |
| Vitamin B3 | 5 mg |
| Vitamin B5 | 5 mg |
| Biotin | 100 mg |
| Pyruvate | 200 mg |
| Whey protein | 5 g |
| Raisin puree | 200 mg |
| Honey | 50 mg |
| MCT | 50 mg |
| Deionized water | 5 cc |
| Cinnamon powder | 10 mg |
| Butter | 150 mg |

Example 19

Skeletal bone loss is associated with inflammatory processes. It is believed that the statin category of drugs ameliorates osteoporosis by an anti-inflammatory mechanism. Pro-inflammatory transcription factors AP-1 and NFKB play a role. By limiting reductive stress and its subsequent effects upon AP-1 and NFKB, MUT acts in a similar anti-inflammatory fashion.

Prior art has stressed calcium supplementation as the cornerstone of a successful program for bone health. While calcium deficiency may certainly be a risk factor for osteopenia, bone disorders are not necessarily cured by supplemental calcium.

Examination of evolutionary nutrition and its effects upon bone metabolism helps explain issues of bone health. Neanderthal nutritional modeling studies arrive at similar conclusions to those of direct studies of modern day hunter-gather cultures consuming their native diets. When interpreted from the perspective of dietary intake and its effect upon nutritional acid load to the body, great differences are noted between our "ancestral" diet and current dietary intake. Modern food choices expose us to a large acid load, day after day, throughout our lifetimes. In comparison, our evolutionarily based diet delivered a neutral, or even slightly alkaline, load. This contrasts starkly with modern cuisine. This situation is at nutritional odds with our genetic legacy and -metabolic impacts.

The effect of chronic acid loading is to lower the pH of the blood. The pH in blood is metabolically regulated in a healthy individual and is kept within a narrow range. This is necessary because of the severe consequences of even minor pH changes. The appropriate bodily response to an acid load is to buffer the pH change. This buffering effect tends to restore pH to the normal range. This is a beneficial physiologic action and forms the basis for regulation of the pH in blood.

There is, however, a dark side to this process if it continues for an extended period of time. This is easily understood if the processes responsible for this buffering are investigated. The largest pool of acid buffer in the body is its carbonate reservoir. This resides almost exclusively in our bone mass where it is anchored by the mineral matrix. Calcium is one of these binding agents. As carbonate leaves the bone matrix, on its way to the blood stream where the pH buffering occurs, calcium is an unwilling participant in the same journey. This process, the simultaneous loss of bone calcium and carbonate, over time induces a slow, gradual progressive loss of bone mass and manifests itself as osteoporosis.

The calcium that leaves the bone reservoir makes its way to the blood stream. Just as blood pH is carefully regulated, so is the blood calcium level. To prevent any significant rise in the blood calcium level, renal compensatory mechanisms are activated. These involve the loss of calcium in the urine. In this manner, the majority of the calcium lost from bone ends up in the urine. From this perspective it is easy to see why calcium supplementation is not the treatment of choice for osteoporosis. At best, it might only prevent calcium deficiency from developing. Indeed, many individuals on high dose calcium supplementation protocols develop calcium stones in their urinary tract.

Chronic nutritional metabolic acidosis may be viewed as an irritant to the body, much like infection or inflammation. The most logical treatment for osteoporosis is nutritional. Inappropriate dietary choices cause the calcium loss, so appropriate dietary choices may prevent the calcium loss. As explained above, this does not include high-dose calcium supplementation.

When for any reason appropriate dietary choices are impractical, then a backup plan that otherwise addresses the causative mechanism is indicated. This includes the use of dietary supplements that correct the diet-induced metabolic acidosis and its deleterious effects upon bone. Included in a preferred formulation is a potassium salt having an anion that is either bicarbonate or a metabolic precursor, such as citrate. Potassium bicarbonate ($KHCO_3$) may be taken easily, is well tolerated and immediately corrects the metabolic acidosis. This obviates the need for carbonate from bone to act as a buffer and physiologically remedies the problem of acidosis related bone loss.

A more complete program includes an MUT formulation to treat the inflammatory component of the disorder. Such a composition includes a combination of MUT agents already discussed in combination with potassium bicarbonate or citrate. Calcium and/or vitamin D or an analog are optionally included. The chosen agents should be well tolerated orally, complement calcium metabolism, have a good safety profile, and be active in bone tissue. Such a composition is listed below. A daily dose (which may be taken in divided doses) includes:

| | |
|---|---|
| $KHCO_3$ | 6 g |
| Serine | 100 mg |
| Alpha lipoic acid | 100 mg |
| B6 | 50 mg |
| B12 | 1 mg |
| Folate | 1 mg |
| Choline | 250 mg |
| Carnitine | 300 mg |
| TMG | 500 mg |
| ALC | 300 mg |

It optionally includes:

| | |
|---|---|
| Vitamin D | 400 IU |
| Calcium (chelate) | 1000 mg |

This combination is applicable in numerous food products including, but not limited to, milk or milk products, juices, shakes, salad dressing, gravies, sauces, nutritional bars, protein powders, and any other palatable food products.

Embodiments in accordance with the invention have been described herein mainly with reference to human physiology and metabolism. The invention is generally useful and widely applicable in mammalian physiology and veterinary medicine. Examples of useful applications include enhancement of athletic performance in greyhounds or racehorses, enhanced and prolonged fertility in breeding stock, and health maintenance in household pets.

It should be understood that the specific formulations and methods described herein are exemplary and should not be construed to limit the invention, which will be described in the claims below. Further, it is evident that those skilled in the art may now make numerous uses and modifications of the specific embodiments described, without departing from the inventive concepts. Also, the invention contemplates that formulations in accordance with the invention may be made of many other combinations of MUT agents than those described above and claimed below. There are many other variations of clinical and metabolic situations, specific methods of addressing such situations, and MUT formulations and compositions than can be included in a document such as this. Consequently, the invention is to be construed as embracing each and every novel feature and novel combination of features present in and/or possessed by the compositions and methods described and by their equivalents.

What is claimed as new and desired to be protected by Letters Patent of the United States is:

1. A method for modulating electron flux to reduce aging of skin of a human, said method comprising applying locally on the skin, for a therapeutically effective period, a composition comprising agents in the following portions: 2 parts of R alpha lipoic acid; 1 part of coenzyme Q10; 1 part of TMG; 1 part of carnitine; 3 parts of phosphatidyl choline; 1 part of nicotinamide; 1 part of glycerylphosphorylcholine; 0.6 parts of etidronic acid; 0.5 parts of green tea leaf extract; 4 parts of vitamin E oil; 4 parts of CLA; 4 parts of medium chain triglycerides; 0.5 parts of kojic acid; 1 part of retinyl palmitate; 0.5 parts of niacin; 0.5 parts of folate; 0.1 parts of pyridoxine; 0.1 parts of glycine; 0.2 parts of arginine; 20 parts of aloe vera gel; and 24 parts of jojoba oil.

* * * * *